(12) United States Patent
Kinsho et al.

(10) Patent No.: US 11,530,176 B2
(45) Date of Patent: Dec. 20, 2022

(54) PROCESSES FOR PREPARING A 2-(1,2,2-TRIMETHYL-3-CYCLOPENTENYL)-2-OXOETHYL CARBOXYLATE COMPOUND AND HYDROXYMETHYL 1,2,2-TRIMETHYL-3-CYCLOPENTENYL KETONE, AND A HALOMETHYL (1,2,2-TRIMETHYL-3-CYCLOPENTENYL) KETONE COMPOUND

(71) Applicant: Shin-Etsu Chemical Co., Ltd., Tokyo (JP)

(72) Inventors: Takeshi Kinsho, Niigata (JP); Tomohiro Watanabe, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 279 days.

(21) Appl. No.: 17/071,013

(22) Filed: Oct. 15, 2020

(65) Prior Publication Data

US 2021/0114960 A1 Apr. 22, 2021

(30) Foreign Application Priority Data

Oct. 16, 2019 (JP) .............................. JP2019-189784

(51) Int. Cl.
| | | |
|---|---|---|
| *C07C 45/41* | (2006.01) | |
| *C07C 45/51* | (2006.01) | |
| *C07C 49/23* | (2006.01) | |
| *C07C 67/10* | (2006.01) | |
| *C07F 7/18* | (2006.01) | |

(52) U.S. Cl.
CPC ............ *C07C 45/41* (2013.01); *C07C 45/513* (2013.01); *C07C 49/23* (2013.01); *C07C 67/10* (2013.01); *C07F 7/188* (2013.01)

(58) Field of Classification Search
CPC ..................................................... C07C 67/10
USPC ........................................................ 568/356
See application file for complete search history.

(56) References Cited

FOREIGN PATENT DOCUMENTS

| RU | 2420507 C1 | 6/2011 |
|---|---|---|
| WO | 2016181413 A1 | 11/2016 |

OTHER PUBLICATIONS

Franco et al. "Novel Approaches for the Management of Mealybug Pests" Biorational Control of Arthropod Pests, Springer, pp. 233-278 (2009).

Millar et al. "Chemistry and Applications of Mealybug Sex Pheromones" Semiochemicals in Pest and Weed Control, Chapter 2, pp. 11-27 (2005).

Ross et al. "Scale insects" Current Biology, 19(5):R184-R186 (2009).

Tabata et al. "Sex pheromone of a coccoid insect with sexual and asexual lineages: fate of an ancestrally essential sexual signal in parthenogenetic females" Journal of the Royal Society Interface, 14:20170027 (11 pages) (2017).

Tabata et al. "Sexual attractiveness and reproductive performance in ageing females of a coccoid insect" Biology Letters, 14:20180262 (5 pages) (2018).

Zou et al. "Chemistry of the pheromones of mealybug and scale insects" Natural Product Reports, 32:1067-1113 (2015).

Extended European Search Report corresponding to European Patent Application No. 20201535.0 (6 pages) (dated Feb. 17, 2021).

Il'Ina et al. "Reactions of Allyl Alcohols of the Pinane Series and of Their Epoxides in the Presence of Montmorillonite Clay" Helvetica Chimica Acta, 90(2):353-368 (2007).

Tabata et al. "Sex pheromone of the aerial root mealybug, *Pseudococcus baliteus*: A unique monoterpenoid containing an α-hydroxyketone moiety" Tetrahedron Letters, 61(17):1-5 (2020).

*Primary Examiner* — Ana Z Muresan

(74) *Attorney, Agent, or Firm* — Myers Bigel, P.A.

(57) ABSTRACT

A process for preparing a 2-(1,2,2-trimethyl-3-cyclopentenyl)-2-oxoethyl carboxylate compound of the following general formula (6), wherein R represents a monovalent hydrocarbon group having 1 to 9 carbon atoms, the process comprising esterifying a 2-(1,2,2-trimethyl-3-cyclopentenyl)-2-oxoethyl compound of the following general formula (5), wherein X represents a hydroxyl group or a halogen atom, to form the 2-(1,2,2-trimethyl-3-cyclopentenyl)-2-oxoethyl carboxylate compound (6).

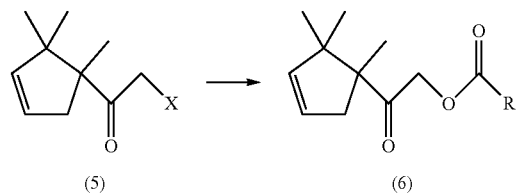

(5)　　　　　　　(6)

5 Claims, 3 Drawing Sheets

PROCESSES FOR PREPARING A 2-(1,2,2-TRIMETHYL-3-CYCLOPENTENYL)-2-OXOETHYL CARBOXYLATE COMPOUND AND HYDROXYMETHYL 1,2,2-TRIMETHYL-3-CYCLOPENTENYL KETONE, AND A HALOMETHYL (1,2,2-TRIMETHYL-3-CYCLOPENTENYL) KETONE COMPOUND

CROSS-REFERENCE TO RELATED APPLICATION

This U.S. nonprovisional application claims priority to Japanese Application No. 2019-189784 filed Oct. 16, 2019, the entire contents of which are incorporated herein by reference.

TECHNICAL FIELD

The present invention relates to processes for preparing a 2-(1,2,2-trimethyl-3-cyclopentenyl)-2-oxoethyl carboxylate compound and hydroxymethyl 1,2,2-trimethyl-3-cyclopentenyl ketone. The present invention relates also to a halomethyl (1,2,2-trimethyl-3-cyclopentenyl) ketone compound.

BACKGROUND ART

Insect sex pheromones are biologically active substances which usually have a function of females to attracting males, and exhibit high attracting activity in a small amount. Many applications for managing pests with sex pheromones have been devised and carried out. For instance, sex pheromones are widely used as a means for forecasting outbreaks of pests or confirming geographic spread (invasion into a specific area), and as a means for controlling pests. Widely used methods of controlling pests are a mass trapping method, a lure & kill or attract & kill method, a lure & infect or attract & infect method, and a mating disruption method.

Mealybugs (Hemiptera: Pseudococcidae) are small insects that feed on plant sap and some members are notorious agricultural pests that parasitize and severely damage crop and fruit plants. Because mealybugs are often hard to find on plant tissues to which they are adhered, it is sometimes difficult to eliminate them during quarantine of live plant materials. Traps baited with sex pheromones that strongly and species-selectively attract pests would be useful for detecting and monitoring these targets in the global plant trade.

Adult female mealybugs hardly ever move, because they lack wings and have retrogressed legs. In contrast, adult males are winged but tiny and fragile with a limited lifespan of a few days at most because they do not feed as adults (Non-Patent Literatures 1 and 2 listed below). Sex pheromones emitted by sedentary females are essential for attracting ephemeral males and are considered to be under strong selection pressure to facilitate mating and reproduction by serving as a key navigation tool for copulation (Non-Patent Literatures 3 and 4 listed below). In fact, mealybug pheromones are highly divergent with strictly species-specific structures (Non-Patent Literatures 5 and 6 listed below). Thus, mealybug pheromones are both a useful tool for pest management and an intriguing model for studying the diversification of chemical communication channels in insects.

*Pseudococcus baliteus* (common name: aerial root mealybug; hereinafter referred to as "ARMB") was first described from the Philippines, have spread in the Ryukyu Islands including Ishigaki Island in Japan, and is a very problematic pest in quarantine. Pheromone of this species has remained unidentified. There is a high demand for elucidation of the pheromone.

LIST OF THE PRIOR ART

[Non-Patent Literature 1] J. C. Franco, A. Zada, Z. Mendel, in: Biorational Control of Arthropod Pests, Springer, Dordrecht, 2009, pp. 233-278.

[Non-Patent Literature 2] L. Ross, D. M. Shuker, Curr. Biol. 19 (2009) R184-R186.

[Non-Patent Literature 3] J. Tabata, R. T. Ichiki, C. Moromizato, K. Mori, J. R. Soc. Interface 14 (2017) 20170027.

[Non-Patent Literature 4] J. Tabata, M. Teshiba, Biol. Lett. 14 (2018) 20180262.

[Non-Patent Literature 5] J. G. Millar, K. M. Daan, J. S. McElfresh, J. A. Moreira, W. J. Bentley, in: R. J. Petroski, M. R. Tellez, R. W. Behle (Eds.), Semiochemicals in Pest and Weed Control, American Chemical Society, Washington D.C., 2005, pp. 11-27.

[Non-Patent Literature 6] Y. Zou, J. G. Millar, Nat. Prod. Rep. 32 (2015) 1067-1113.

SUMMARY OF THE INVENTION

The present invention aims to provide processes for preparing a pheromone compound of ARMB, whose chemical structure has been now identified, and analogues thereof and to provide an intermediate useful in preparation of the pheromone compound.

The present inventors have isolated and identified a sex pheromone of ARMB and estimated its structure. The present inventors have then synthesized a compound having the estimated structure and confirmed its structure. The present inventors finally have carried out bioactivity tests using the synthesized compound and determined the structure of the sex pheromone including its stereochemistry.

The present inventors have found that a 2-(1,2,2-trimethyl-3-cyclopentenyl)-2-oxoethyl carboxylate compound, which is a sex pheromone of the ARMB, i.e., 2-(1,2,2-trimethyl-3-cyclopentenyl)-2-oxoethyl carboxylate compound including (S)-2-(1,2,2-trimethyl-3-cyclopentenyl)-2-oxoethyl (S)-2-methylbutyrate, may be efficiently prepared from a 2-(1,2,2-trimethyl-3-cyclopentenyl)-2-oxoethyl compound and thus completed the present invention.

According to one aspect of the present invention, there is provided a process for preparing a 2-(1,2,2-trimethyl-3-cyclopentenyl)-2-oxoethyl carboxylate compound of the following general formula (6):

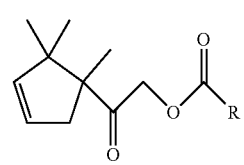

(6)

wherein R represents a monovalent hydrocarbon group having 1 to 9 carbon atoms, the process comprising:

esterifying a 2-(1,2,2-trimethyl-3-cyclopentenyl)-2-oxoethyl compound of the following general formula (5):

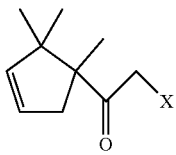

(5)

wherein X represents a hydroxyl group or a halogen atom, to form the 2-(1,2,2-trimethyl-3-cyclopentenyl)-2-oxoethyl carboxylate compound (6).

According to an aspect of the present invention, there is provided the process for preparing the 2-(1,2,2-trimethyl-3-cyclopentenyl)-2-oxoethyl carboxylate compound (6), wherein the esterification is carried out with a halomethyl (1,2,2-trimethyl-3-cyclopentenyl) ketone compound of the following general formula (7):

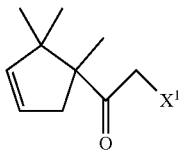

(7)

wherein $X^1$ represents a halogen atom,
and a carboxylic acid compound of the following general formula (8):

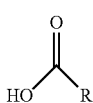

(8)

wherein R represents a monovalent hydrocarbon group having 1 to 9 carbon atoms.

According to another aspect of the present invention, there is provided a process for preparing hydroxymethyl 1,2,2-trimethyl-3-cyclopentenyl ketone of the following formula (3):

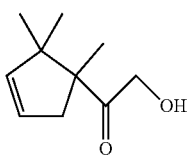

(3)

the process comprising
the aforesaid process for preparing the aforesaid 2-(1,2,2-trimethyl-3-cyclopentenyl)-2-oxoethyl carboxylate compound (6), and
subjecting the 2-(1,2,2-trimethyl-3-cyclopentenyl)-2-oxoethyl carboxylate compound (6) to hydrolysis and/or alcoholysis to form the hydroxymethyl 1,2,2-trimethyl-3-cyclopentenyl ketone (3).

According to another aspect of the present invention, there is further provided a halomethyl (1,2,2-trimethyl-3-cyclopentenyl) ketone compound of the following general formula (7):

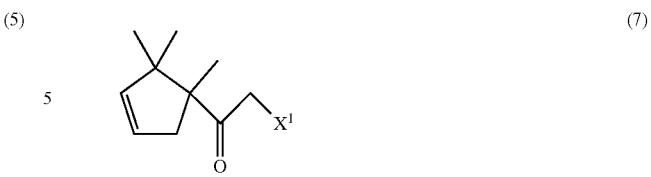

(7)

wherein $X^1$ represents a halogen atom.

According to the present invention, it is possible to efficiently prepare the 2-(1,2,2-trimethyl-3-cyclopentenyl)-2-oxoethyl carboxylate compound such as (S)-2-(1,2,2-trimethyl-3-cyclopentenyl)-2-oxoethyl (S)-2-methylbutyrate, which is a sex pheromone of ARMB.

DETAILED DESCRIPTION OF THE PREFERRED EMBODIMENTS

Embodiments of the present invention will be described in detail below. It should be understood that the present invention is not limited to or by the embodiments.

In the intermediates, the reagents and the target compounds represented by the chemical formulae in the present specification, there may be some stereoisomers such as enantiomers (optical isomers) or diastereoisomers. Unless otherwise stated, each chemical formula shall be interpreted to represent all of these isomers. The isomer may be used either alone or in combination thereof.

Identification of a pheromone of ARMB will be first described. Isolation and identification of the pheromone of ARMB The pheromone of ARMB was isolated and identified (estimating the structure) as described below.

First, headspace volatiles from virgin ARMB females reared on a squash fruit in a glass chamber (1 L) were drawn in a flow rate of 1 L/min and collected in a HayeSepQ adsorbent (1 g). Every 3 or 4 days, the volatiles were extracted with 15 mL of n-hexane and concentrated in an evaporator at room temperature. The concentrate was stored at −20° C. 294,000 female day equivalents were collected. The crude extract thus obtained was analyzed by a gas chromatograph (GC) equipped with an electroantennographic detector (EAD). A single compound (1) having a Kovat's index of 2185 in a DB-23 column was found to induce an antenna response, which is thus to be a candidate pheromone.

Figure 1A:
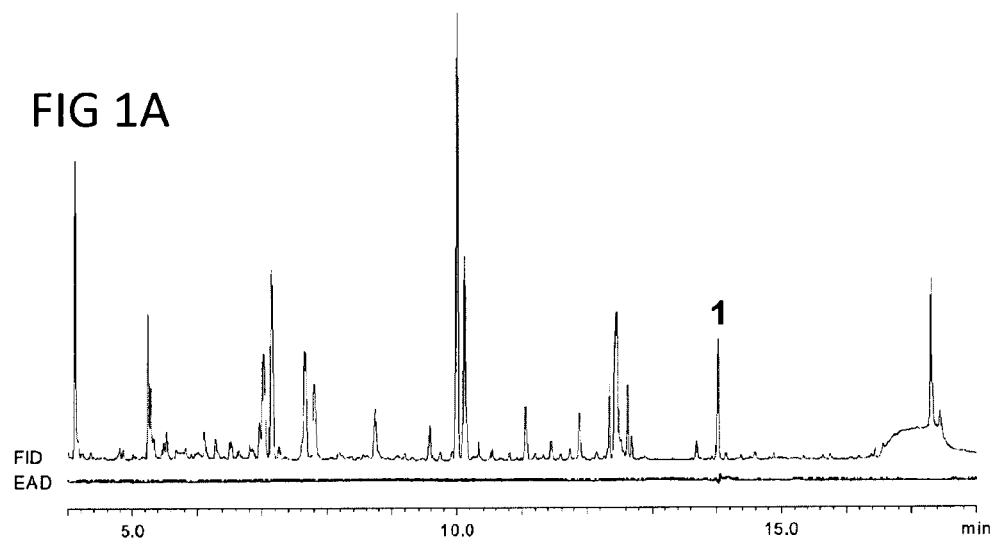
FIG. 1A shows a chromatogram of GC-FID (Gas Chromatography-Flame Ionization Detection) and GC-EAD (a gas chromatograph (GC) equipped with an electroantennographic detector (EAD)) of an extract of headspace volatiles from virgin females of Pseudococcus baliteus.

FIG. 1(a) shows a chromatogram of GC-FID and GC-EAD of the extract of the headspace volatilest from females of *Pseudococcus baliteus*.

Figure 1B:
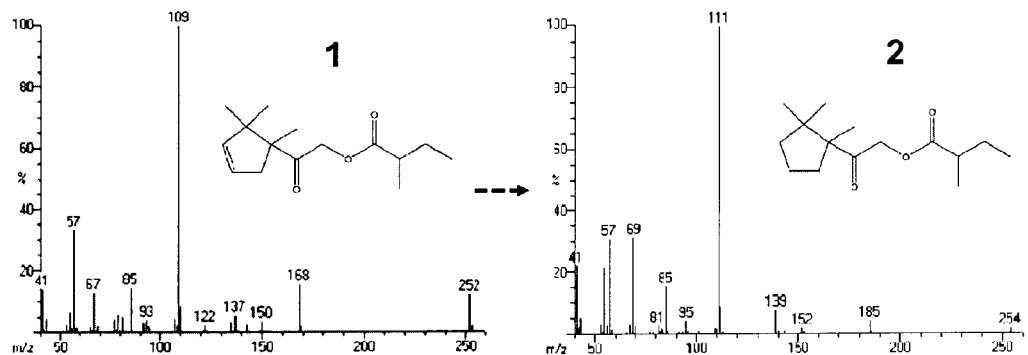
FIG. 1B shows mass spectra of naturally occurring compound (1), hydrogenation product (2) from compound (1)
Figure 1C:
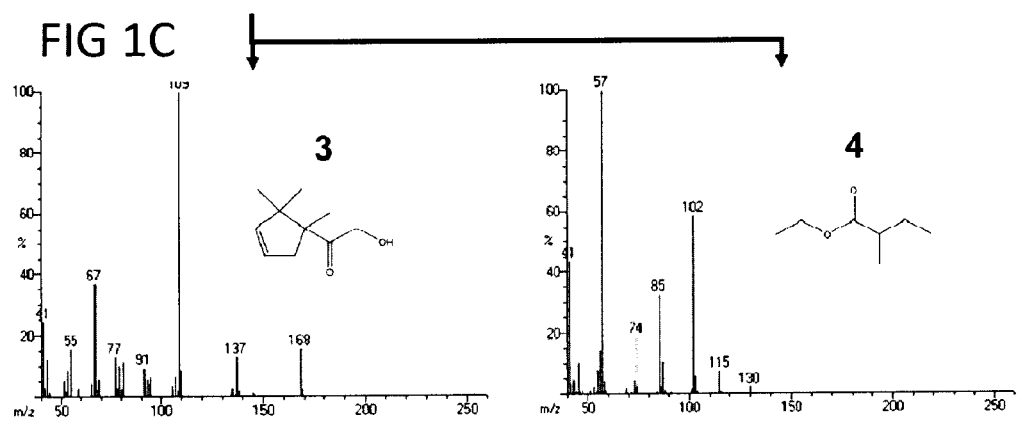
FIG. 1C shows the mass spectra of basic ethanolysis products (3) and (4) from compound (1).

Next, compound (1) was analyzed in a Gas Chromatography-Mass Spectrometer (GC-MS). In high-resolution mass spectrum in electron impact ionization (EI) at 70 eV, compound (1) had a molecular formula of $C_{15}H_{24}O_3$ (found 252.17804; theoretically 252.17255), which suggests four degree of unsaturation (double bond or ring structure). Compound (1) was subjected to a microscale hydrogenation to form a single product, compound (2). Compound (2) showed a molecular ion peak of m/z 254, indicating the presence of one double bond. Base peaks of fragments of compounds (1) and (2) in their mass spectra were observed at 109 and 111, respectively, which indicates that compound (1) has a trimethylcyclopentenyl ($C_8H_{13}$) moiety. Basic ethanolysis and transesterification of compound (1) gave two peaks corresponding to compound (3) and compound (4). Their molecular ions were observed at m/z 168 and 130, respectively. These mass spectra are shown in FIG. 1 (b). EI-MS and GC retention time of compound (4) indicate that compound (1) is an ester compound from 2-methylbutanoic acid and an alcohol having a trimethylcyclopentene structure.

About 0.1 mg of compound (1) was purified to a purity of more than 99% by a preparative GC and a preparative liquid chromatograph (LC), which was then dissolved in 35 μl of $C_6D_6$ and analyzed by nuclear magnetic resonance (NMR). The $^1$H-NMR spectrum showed the presence of two olefinic protons and five sets of methyl protons. $^{13}$C-NMR signals with distortionless enhanced by polarization transfer (DEPT) analysis indicated the presence of four quaternary carbon atoms including two carbonyl carbon atoms.

One of the signals (175.5 ppm) of the carbonyl carbon atoms is characteristic of a carboxylate ester, suggesting the presence of a carboxylate ester. Heteronuclear single-quantum coherence (HSQC) and heteronuclear multiple-bond coherence (HMBC) analyses showed that this carbonyl carbon atom was in coupling with a methine proton (2.46 ppm) and, further, coupling with a methyl group (1.20 ppm, d, J=6.6 Hz) and a set of geminal protons (1.46 ppm and 1.82 ppm), and that the set of geminal protons correlate with another methyl group (0.96 ppm, t, J=6.0 Hz). These results indicate that compound (1) is a 2-methylbutanoate ester (2-methylbutyrate), which is consistent with the expectation from the product of the microscale transesterification. The other signal (205.1 ppm) of the carbonyl carbon atom correlates with signals originated from a set of doublet protons at 4.54 and 4.60 ppm (J=17.4 Hz). This correlation is characteristic of protons adjacent to an oxygen atom of an ester. The other moiety corresponding to singlet signals (0.91, 0.94, and 0.95 ppm) originating from two quaternary carbon atoms and three sets of methyl protons is thought to form a trimethyl cyclopentenyl structure. $^1$H-NMR decoupling analysis revealed that two olefinic protons (5.11 ppm, ddd, J=1.8, 2.4, 5.4 Hz; and 5.29 ppm, ddd, J=1.8, 2.4, 5.4 Hz) were in coupling with another set of geminal protons (1.71 ppm, ddd, J=1.8, 2.4, 16.8 Hz; and 2.92 ppm, ddd, J=1.8, 2.4, 16.8 Hz). These results suggest that the ring structure is a 1,2,2-trimethyl-3-cyclopentenyl or 1,2,2-trimethyl-4-cyclopentenyl structure. The HMBC and nuclear Overhauser effect (NOE) patterns indicate that the former would be more reasonable. From the aforesaid results, compound (1) is 2-(1,2,2-trimethyl-3-cyclopentenyl)-2-oxoethyl 2-methylbutyrate of the following formula (1), and compound (2) is 2-(1,2,2-trimethylcyclopentyl)-2-oxoethyl 2-methylbutyrate of the following formula (2).

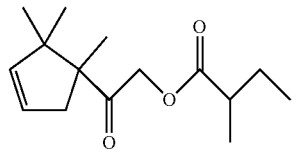

(1)

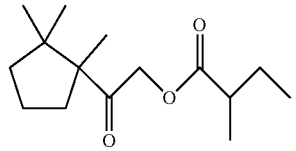

(2)

2-(1,2,2-Trimethyl-3-cyclopentenyl)-2-oxoethyl 2-methylbutyrate (1) has each one asymmetric carbon atom in each of the hydroxy ketone moiety and the carboxylate moiety and thus will have four stereoisomers that are different in configuration. In other words, compound (1) may comprise the following four stereoisomers: (R)-2-(1,2,2-trimethyl-3-cyclopentenyl)-2-oxoethyl (R)-2-methylbutyrate of the following formula (R,R)-(1):

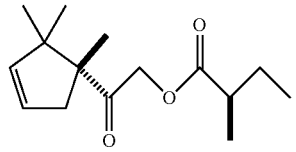

(R,R)-(1)

(R)-2-(1,2,2-trimethyl-3-cyclopentenyl)-2-oxoethyl (S)-2-methylbutyrate of the following formula (R,S)-(1):

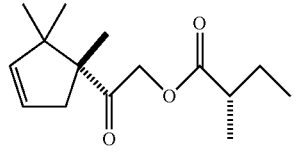

(R,S)-(1)

(S)-2-(1,2,2-trimethyl-3-cyclopentenyl)-2-oxoethyl (R)-2-methylbutyrate of the following formula (S,R)-(1):

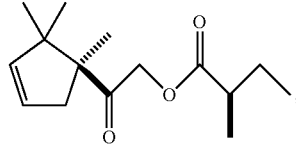

(S,R)-(1)

and (S)-2-(1,2,2-trimethyl-3-cyclopentenyl)-2-oxoethyl (S)-2-methylbutyrate of the following formula (S,S)-(1):

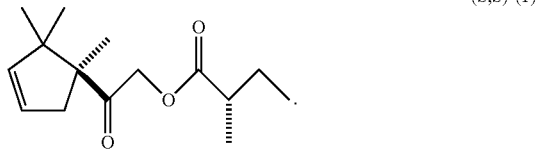

(S,S)-(1)

Synthesis of all of the Four Stereoisomers

The present inventors have synthesized (R)-methyl 1,2,2-trimethyl-3-cyclopentenyl ketone and (S)-methyl 1,2,2-trimethyl-3-cyclopentenyl ketone from (+)-camphor and (−)-camphor (both, 100% ee), respectively. Each of the products were reacted with (R)-2-methylbutanoic acid or (S)-2-methylbutanoic acid (89.3% ee or 98.6% ee, respectively) to obtain all of the four stereoisomers of compound (1): (R,R)-(1), (R,S)-(1), (S,R)-(1), and (S,S)-(1).

The present inventors have also synthesized both enantiomers of hydroxymethyl 1,2,2-trimethyl-3-cyclopentenyl ketone: (R)-(3) and (S)-(3).

A method of synthesizing compound (1) will be described in detail in the Examples below.

Determination of Stereochemistry of ARMB Pheromone

The stereochemistry of the naturally occurring compound was determined by comparing spectral data of a synthetic product, the naturally occurring compound, and derivatives thereof, as described below.

Figure 2:
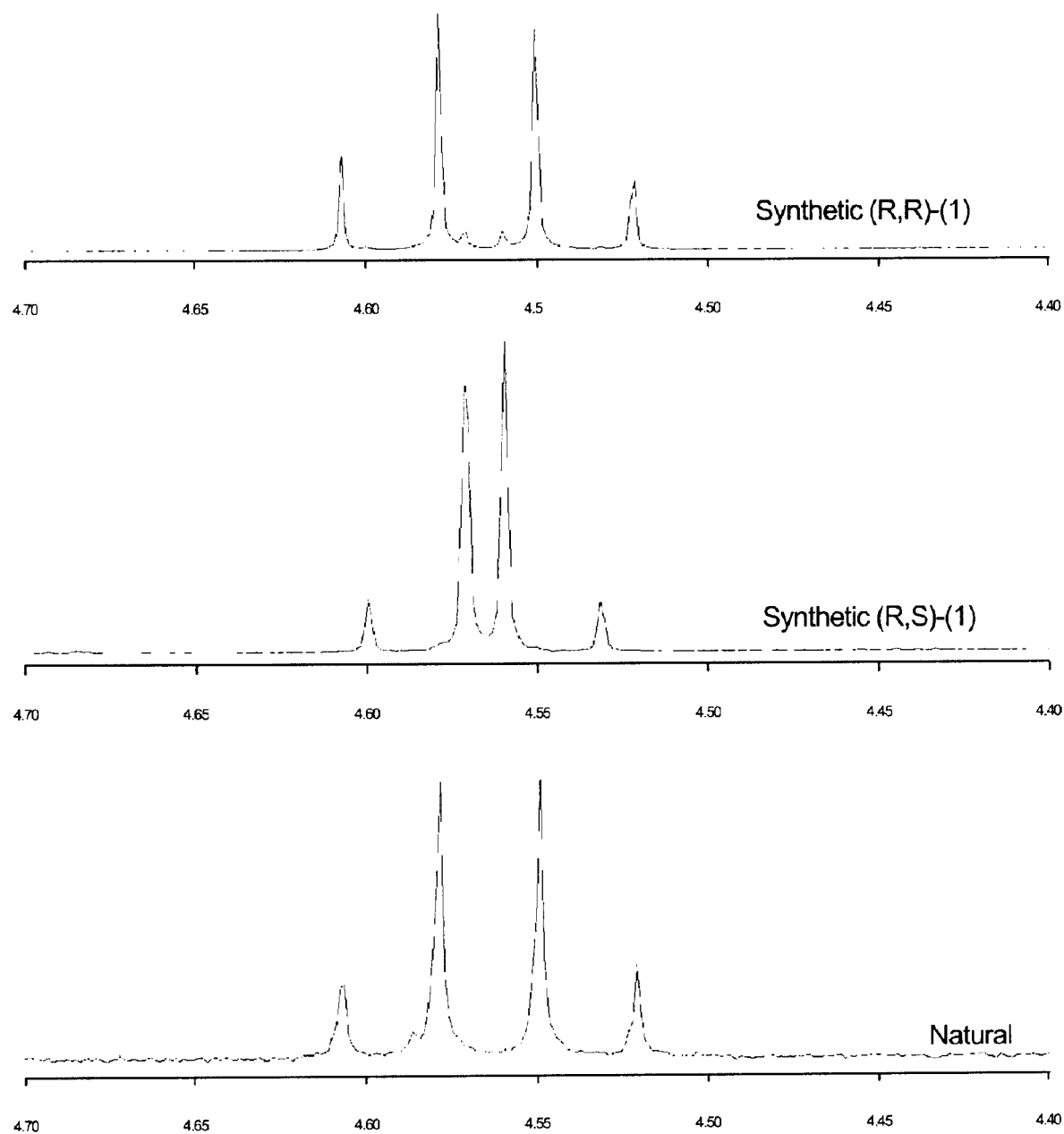
FIG. 2 shows $^1$H-NMR signals of methylene protons adjacent to the keto groups in a synthetic compound (1) and a naturally occurring compound (1). In this Figure, "Synthetic" means a synthetic compound, and "Natural" means a naturally occurring compound.

As seen in FIG. 2, the $^1$H-NMR chemical shift and coupling constant of methylene protons adjacent to the keto groups in the naturally occurring compound (1) are same as those of synthetic (R*,R*)-(1), wherein (R*,R*)-(1) represents (R,R)-(1) or (S,S)-(1), but are different from those of (R*, S*)-(1), wherein (R*,S*)-(1) represents (R,S)-(1) or (S,R)-(1).

In the GC analysis with a chiral resolution column, β-DEX™ 120, (R)-(3) and (S)-(3) showed retention times of 25.2 min and 25.3 min, respectively. The latter retention time was consistent with that of the hydrolysis product from the naturally occurring compound (1).

Synthetic (S,S)-(1) and the naturally occurring compound (1) have angles of rotation of $[\alpha]_D^{24}$ −65° (c=1.01, CHCl$_3$) and $[\alpha]_D^{25}$ −71° (c=0.0135, hexane), respectively. Both of these are levorotatory. This supports that the naturally occurring compound has absolute configuration of (S,S).

Attracting Activities of the Four Synthesized Stereoisomers

Figure 3:
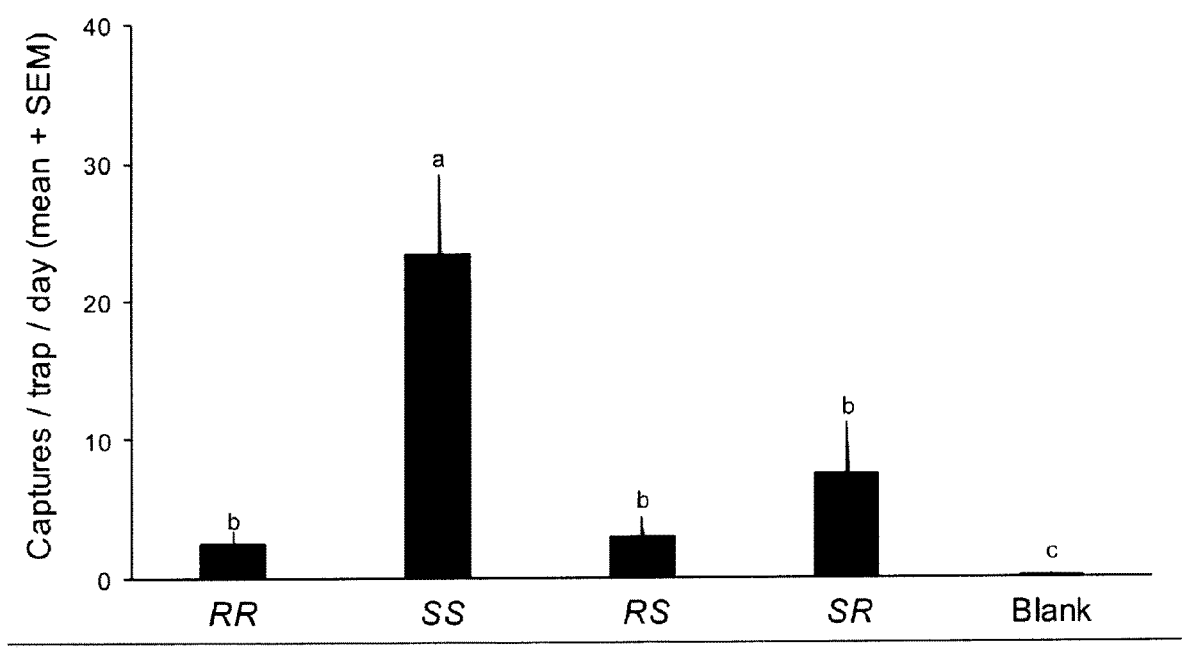
FIG. 3 shows a response of male Pseudococcus baliteus to the synthetic compound (1).

FIG. 3 shows the results of bioactivity tests in a greenhouse on attracting activities of the four synthesized stereoisomers of compound (1). In FIG. 3, "Blank" represents a case of solvent (hexane) alone. "Captures/trap/day (mean+SEM)" on the vertical axis in the graph of FIG. 3 represents the number of captured insects per day (mean+standard error). Lowercase letters, a, b, and c represent statistically significant differences in ANOVA followed by Tukey-Kramer HSD test.

The (S,S)-isomer, which has the natural absolute configuration of compound (1), had the highest attracting power for males. The (S,R)-isomer attracted some males. It is unclear whether the males were attracted by the (S,R)-isomer itself or by the (S,S)-isomer which was contained in a small amount. The other isomers showed low activities.

The present inventors have concluded that (S,S)-(1) is the pheromone of ARMB, or *Pseudococcus baliteus*, taking into consideration the combination of the results of the chemical analyses and the results of the bioactivity tests.

The monoterpenoid having an α-hydroxy ketone moiety is an extremely unique example of pheromones of mealybugs. Relatively simple α-hydroxy ketones having a secondary hydroxyl group are known as aggregation pheromones that are produced by males of some species of long-horned beetles. However, the structure having a primary alcohol moiety having a keto group (ketonic carbonyl group) at α-position, like compound (1), is extremely rare among insect pheromones.

The present invention will be described in details hereinafter.

First, 2-(1,2,2-trimethyl-3-cyclopentenyl)-2-oxoethyl compound of the following general formula (5) will be described,

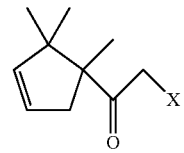

(5)

wherein X represents a hydroxyl group or a halogen atom.

When X is a halogen atom, the 2-(1,2,2-trimethyl-3-cyclopentenyl)-2-oxoethyl compound is a halomethyl 1,2,2-trimethyl-3-cyclopentenyl ketone compound of the following general formula (7):

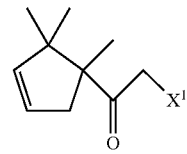

(7)

wherein X$^1$ represents a halogen atom.

Examples of the halogen atom X$^1$ include a chlorine atom, a bromine atom, and an iodine atom, with chlorine and bromine atoms being particularly preferred in view of the availability of raw materials, and the reactivity and stability of intermediates.

Examples of the halomethyl 1,2,2-trimethyl-3-cyclopentenyl ketone compound (7) include a (S)-halomethyl 1,2,2-trimethyl-3-cyclopentenyl ketone compound of the following general formula (S)-(7), (R)-halomethyl 1,2,2-trimethyl-3-cyclopentenyl ketone compound of the following general formula (R)-(7), and the racemate and scalemic mixtures thereof,

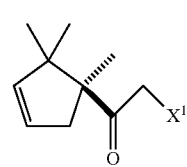

(S)-(7)

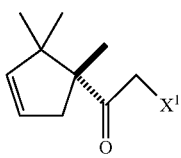

(R)-(7)

wherein X¹ represents a halogen atom.

Specific examples of the (S)-halomethyl 1,2,2-trimethyl-3-cyclopentenyl ketone compound (S)-(7) include (S)-chloromethyl 1,2,2-trimethyl-3-cyclopentenyl ketone, (S)-bromomethyl 1,2,2-trimethyl-3-cyclopentenyl ketone, and (S)-iodomethyl 1,2,2-trimethyl-3-cyclopentenyl ketone.

Specific examples of the (R)-halomethyl 1,2,2-trimethyl-3-cyclopentenyl ketone compound (R)-(7) include (R)-chloromethyl 1,2,2-trimethyl-3-cyclopentenyl ketone, (R)-bromomethyl 1,2,2-trimethyl-3-cyclopentenyl ketone, and (R)-iodomethyl 1,2,2-trimethyl-3-cyclopentenyl ketone.

Halomethyl 1,2,2-trimethyl-3-cyclopentenyl ketone compound (7) may be produced by halogenation of the methyl group adjacent to the carbonyl group of methyl 1,2,2-trimethyl-3-cyclopentenyl ketone (9), as shown in the following chemical reaction formula,

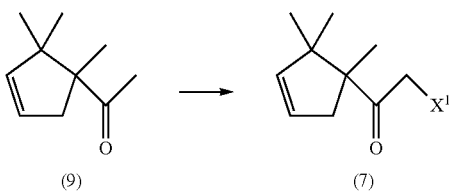

(9)                    (7)

wherein X¹ represents a halogen atom.

Examples of the methyl 1,2,2-trimethyl-3-cyclopentenyl ketone (9) include (S)-methyl 1,2,2-trimethyl-3-cyclopentenyl ketone of the following formula (S)-(9), (R)-methyl 1,2,2-trimethyl-3-cyclopentenyl ketone of the following formula (R)-(9), and the racemate and scalemic mixtures thereof.

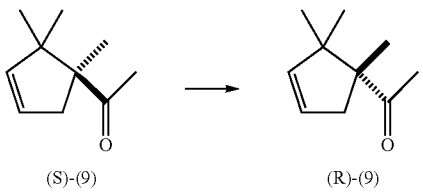

(S)-(9)                    (R)-(9)

Methyl 1,2,2-trimethyl-3-cyclopentenyl ketone (9) may be synthesized from camphor (or 1,7,7-trimethylbicyclo [2.2.1]heptan-2-one), for instance, according to the method described in W. C. Agosta et al., J. Am. Chem. Soc., 90, 7025 (1968), as shown in the following chemical reaction formula.

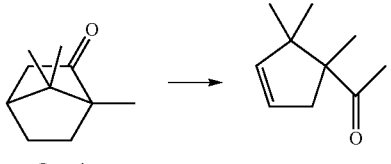

Camphor                    (9)

The starting raw material, camphor, may be either (1R)-(+)-camphor or (1 S)-(−)-camphor. Both of these enantiomers are naturally occurring, pure, and commercially available. (±)-Camphor is a chemically synthesized racemic mixture, and available in a large amount.

Thus, a starting material, camphor, may be chosen, depending on a purpose, from enantiomers, scalemic mixtures containing either enantiomer in excess, and a racemic mixture.

Conversion of a camphor into methyl 1,2,2-trimethyl-3-cyclopentenyl ketone does not involve change of the absolute stereochemistry of the quaternary carbon atom at position 1 of camphor. Accordingly, the stereochemistry of the quaternary carbon atom at position 1 of camphor is maintained in the stereochemistry at position 1 of methyl 1,2,2-trimethyl-3-cyclopentenyl ketone.

The halogenation of the methyl group adjacent to the carbonyl group may be done, using any usual method of α-halogenation of a ketone compound. Examples of the halogenation method include, but are not particularly limited to, a halogenation with a simple substance halogen, a halogenation with an N-halo compound, a halogenation with an onium trihalide compound, and a halogenation with a metal halide.

Examples of the simple substance halogen include chlorine ($C_2$), bromine ($Br_2$), iodine ($I_2$) or, either, bromine chloride (BrCl), and iodine chloride (IC).

The simple substance halogen may be used either alone or in combination thereof, if necessary. The simple substance halogen may be commercially available one.

Examples of the N-halo compound include N-chlorosuccinimide, N-chloroacetamide, N-bromosuccinimide, N-bromoacetamide, 1,3-dibromo-5,5-dimethylhydantoin, dibromoisocyanuric acid, N-bromophthalimide, N,N,N',N'-tetrabromobenzene-1,3-disulfonamide, and poly(N,N'-dibromo-N,N'-ethylene)benzene-1,3-disulfonamide.

Examples of the onium trihalide compound include tetrabutylammonium tribromide, benzyltrimethylammonium tribromide, phenyltrimethylammonium tribromide, pyridinium tribromide, and bromotriphenoxyphosphonium bromide.

The N-halo compound may be used either alone or in combination thereof, if necessary. The N-halo compound may be commercially available one.

Examples of the metal halide include copper (II) bromide and zinc (II) bromide.

The metal halide may be used either alone or in combination thereof, if necessary. The metal halide may be commercially available one.

Methyl 1,2,2-trimethyl-3-cyclopentenyl ketone (9) itself may be used as a substrate of the halogenation reaction. Alternatively, its corresponding enol ether or enol ester may be also used.

Examples of the corresponding enol ether include enol silyl ethers such as a 1,2,2-trimethyl-1-(1-trialkylsilyloxyvinyl)-3-cyclopentene compound, particularly preferably 1,2, 2-trimethyl-1-(1-trimethylsilyloxyvinyl)-3-cyclopentene.

Halomethyl 1,2,2-trimethyl-3-cyclopentenyl ketone compound (7) may be produced also in a halogen exchange reaction of a halomethyl 1,2,2-trimethyl-3-cyclopentenyl ketone compound (7) having a halogen atom different from the envisaged halogen atom with an inorganic halide and/or organic halide having an envisaged halogen atom. Halogen exchange reaction may give chloromethyl 1,2,2-trimethyl-3-cyclopentenyl ketone from bromomethyl 1,2,2-trimethyl-3-cyclopentenyl ketone; bromomethyl 1,2,2-trimethyl-3-cyclopentenyl ketone from chloromethyl 1,2,2-trimethyl-3-cyclopentenyl ketone; iodomethyl 1,2,2-trimethyl-3-cyclopentenyl ketone from chloromethyl 1,2,2-trimethyl-3-cyclopentenyl ketone; and bromomethyl 1,2,2-trimethyl-3-cyclopentenyl ketone from iodomethyl 1,2,2-trimethyl-3-cyclopentenyl ketone.

Examples of the inorganic halide include simple substance halogens, hydrogen halides, and metal halides.

Examples of the organic halide include haloalkanes.

Catalyst may be used in the halogen exchange reaction. Examples of the catalyst include Lewis acids; salts such as tetraalkylammonium halides; metal oxides such as alumina and silica gel; and ion exchange resins.

It has been found that the halomethyl 1,2,2-trimethyl-3-cyclopentenyl ketone compound (7) is more stable than hydroxymethyl 1,2,2-trimethyl-3-cyclopentenyl ketone (3) described below, during storage and in analytical conditions, and that this halomethyl ketone compound is particularly preferred as an intermediate in industrial processes.

Next, hydroxymethyl 1,2,2-trimethyl-3-cyclopentenyl ketone of the following formula (3) will be explained, which compound corresponds to the 2-(1,2,2-trimethyl-3-cyclopentenyl)-2-oxoethyl compound of the general formula (5) wherein X is a hydroxyl group.

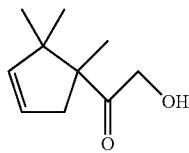

(3)

Hydroxymethyl 1,2,2-trimethyl-3-cyclopentenyl ketone (3) includes (S)-hydroxymethyl 1,2,2-trimethyl-3-cyclopentenyl ketone of the following formula (S)-(3), (R)-hydroxymethyl 1,2,2-trimethyl-3-cyclopentenyl ketone of the following formula (R)-(3), and the racemate and scalemic mixtures thereof.

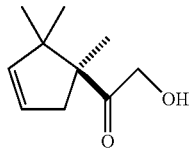

(S)-(3)

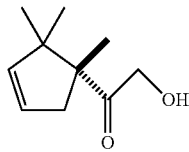

(R)-(3)

Hydroxymethyl 1,2,2-trimethyl-3-cyclopentenyl ketone (3) may be produced by hydroxylation of the methyl group adjacent to the carbonyl group of methyl 1,2,2-trimethyl-3-cyclopentenyl ketone (9), as shown in the following chemical reaction formula.

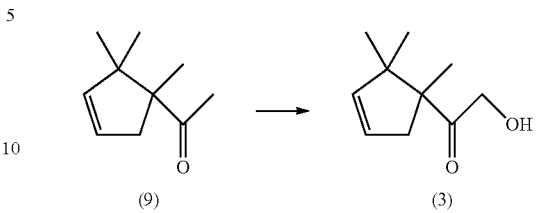

The hydroxylation of the methyl group adjacent to the carbonyl group may be practiced in any known method for α-hydroxylation of a ketone compound such as hydroxylation with a hypervalent iodine reagent, hydroxylation with metallic oxydizing agent, and biochemical hydroxylation with microorganism, but not particularly limited to these.

Methyl 1,2,2-trimethyl-3-cyclopentenyl ketone (9) is already mentioned above.

Examples of the hypervalent iodine reagent include o-iodosobenzoic acid, iodobenzene dicholoride, diacetoxyiodobenzene, bis(trifluoroacetoxy)iodobenzene, iodosylbenzene, 2-iodoxybenzoic acid, and Dess-Martin reagent (1,1,1-triacetoxy-1,1-dihydro-1,2-benziodoxol-3 (1H)-one).

The hypervalent iodine reagent may be used either alone or in combination thereof, if necessary. The hypervalent iodine reagent may be commercially available ones.

Examples of the metallic oxydizing agent include transition metal oxidizing agents such as oxodiperoxy molybdenium-pyridine-hexamethylphosphoramide complex ($MoO_5$—$C_5H_5N$-HMPA) and chromyl chloride ($Cr_2Cl_2$).

The metallic oxydizing agent may be used either alone or in combination thereof, if necessary. The metallic oxydizing agent may be commercially available ones.

Methyl 1,2,2-trimethyl-3-cyclopentenyl ketone itself may be used as a substrate for the hydroxylation. Alternatively, its corresponding enol ether or enol ester may also be used.

Examples of the corresponding enol ether include enol silyl ethers such as a 1,2,2-trimethyl-1-(1-trialkylsilyloxyvinyl)-3-cyclopentene compound, particularly preferably 1,2,2-trimethyl-1-(1-trimethylsilyloxyvinyl)-3-cyclopentene.

Hydroxymethyl 1,2,2-trimethyl-3-cyclopentenyl ketone (3) may be produced by hydrolysis and/or alcoholysis of 2-(1,2,2-trimethyl-3-cyclopentenyl)-2-oxoethyl carboxylate compound of the following general formula (6), as shown in the following chemical reaction formula,

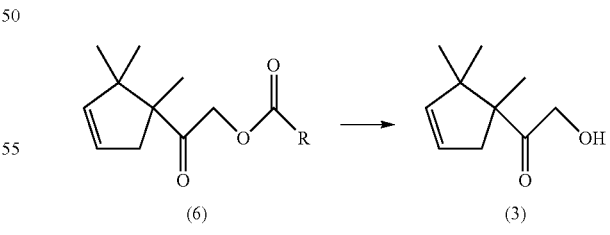

wherein R represents a monovalent hydrocarbon group having 1 to 9 carbon atoms.

Hydroxymethyl 1,2,2-trimethyl-3-cyclopentenyl ketone compound (3) may be synthesized from the pheromone of ARMB compounds or analogues thereof. This method is useful also for industrially synthesizing other analogues.

Hydrolysis is carried out typically using water in the presence of a base.

An amount of water used in the hydrolysis is preferably from 1.0 to 100,000,000 mol per mol of 2-(1,2,2-trimethyl-3-cyclopentenyl)-2-oxoethyl carboxylate compound (6).

The alcoholysis is carried out typically using a lower alcohol having 1 to 3 carbon atoms such as methanol, ethanol, 1-propanol, and 2-propanol, in the presence of a base.

The lower alcohol having 1 to 3 carbon atoms may be used either alone or in combination thereof, if necessary. The lower alcohol having 1 to 3 carbon atoms may be commercially available one.

An amount of the lower alcohol having 1 to 3 carbon atoms used in the alcoholysis is preferably from 1.0 to 100,000,000 mol per mol of 2-(1,2,2-trimethyl-3-cyclopentenyl)-2-oxoethyl carboxylate compound (6).

Examples of the base used in the hydrolysis or alcoholysis include hydroxide salts such as lithium hydroxide, sodium hydroxide, potassium hydroxide, and barium hydroxide; alkoxides such as sodium methoxide, sodium ethoxide, lithium t-butoxide, and potassium t-butoxide; and basic ion exchange resins. The base may be used either alone or in combination thereof, if necessary. The base may be commercially available one.

An amount of the base used is preferably from 0.000001 to 100 mol, more preferably 0.0001 to 1 mol, and even more preferably 0.001 to 1 mol, per mol of the 2-(1,2,2-trimethyl-3-cyclopentenyl)-2-oxoethyl carboxylate compound (6).

A solvent may be used in the hydrolysis or alcoholysis.

Water and the lower alcohols such as methanol, ethanol, 1-propanol, or 2-propanol or mixtures thereof, which are a reactant, may serve also as a solvent. Other examples of the solvent include haloalkanes such as methylene chloride, chloroform, and trichloroethylene; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, and 1,4-dioxane; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoramide.

The solvent may be used either alone or in combination thereof, if necessary. The solvent may be commercially available one.

An amount of the solvent used is preferably from 100 to 1,000,000 mL per mol of the 2-(1,2,2-trimethyl-3-cyclopentenyl)-2-oxoethyl carboxylate compound (6).

A reaction temperature in the hydrolysis or alcoholysis may be selected, depending upon reagents to be used and reaction conditions. The reaction temperature is preferably from −50° C. to a boiling point of a solvent, more preferably from −20 to 150° C. or to a boiling point of a solvent.

A reaction time in the hydrolysis or alcoholysis is preferably from 5 minutes to 240 hours.

It has been found that hydroxymethyl 1,2,2-trimethyl-3-cyclopentenyl ketone (3) is vulnerable to oxidation or decomposition during storage or under analytical conditions.

For instance, it has been found that the hydroxymethyl group of hydroxymethyl 1,2,2-trimethyl-3-cyclopentenyl ketone (3) is oxidized into a formyl group to form a ketoaldehyde compound, 2-(1,2,2-trimethyl-3-cyclopentenyl)-2-oxoacetaldehyde, or the hydroxymethyl group of hydroxymethyl 1,2,2-trimethyl-3-cyclopentenyl ketone (3) is converted into a carboxyl group to form a carboxylic acid, 1,2,2-trimethyl-3-cyclopentene-1-carboxylic acid.

Accordingly, it is required to pay attention in storing and analyzing this hydroxymethyl ketone compound in an industrial process using this hydroxymethyl ketone compound as an intermediate material. It is suggestable to synthesize this hydroxymethyl ketone compound only in an amount as required for a particular purpose such as identification, and not to store the compound in a long period.

Esterification

Next, explained is a step of esterifying the 2-(1,2,2-trimethyl-3-cyclopentenyl)-2-oxoethyl compound (5) to form the 2-(1,2,2-trimethyl-3-cyclopentenyl)-2-oxoethyl carboxylate compound of the following general formula (6), as shown in the following chemical reaction formula.

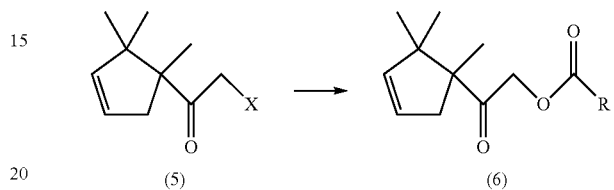

wherein X and R are as defined above.

Examples of the 2-(1,2,2-trimethyl-3-cyclopentenyl)-2-oxoethyl carboxylate compound (6) include (S)-2-(1,2,2-trimethyl-3-cyclopentenyl)-2-oxoethyl carboxylate compound of the following general formula (S)-(6), (R)-2-(1,2,2-trimethyl-3-cyclopentenyl)-2-oxoethyl carboxylate compound of the following general formula (R)-(6), and the racemate and scalemic mixtures thereof.

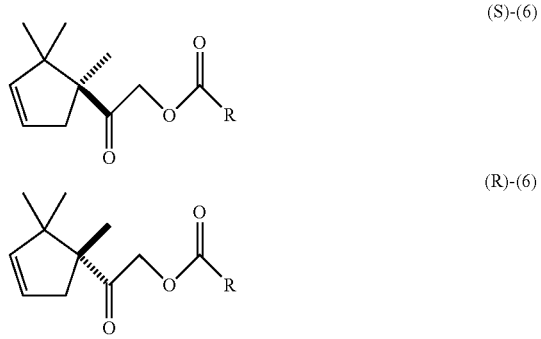

wherein R is as defined above.

R in the 2-(1,2,2-trimethyl-3-cyclopentenyl)-2-oxoethyl carboxylate compound (6) represents a monovalent hydrocarbon group having 1 to 9 carbon atoms.

Examples of the monovalent hydrocarbon group having 1 to 9 carbon atoms include linear alkyl groups such as a methyl group, an ethyl group, an n-propyl group, an n-butyl group, an n-pentyl group, an n-hexyl group, an n-heptyl group, an n-octyl group, and an n-nonyl group; branched alkyl groups such as an isopropyl group, a sec-butyl group, an isobutyl group, an isopentyl group, a 2-pentyl group, a 3-pentyl group, an isohexyl group, and a tert-butyl group; cyclic alkyl groups such as a cyclopentyl group, a cyclohexyl group, a 2-methylcyclopentyl group, and a cyclopentylmethyl group; linear alkenyl groups such as a vinyl group, an ethinyl group, an allyl group, an (E)-1-propenyl group, and a (Z)-1-propenyl group; branched alkenyl groups such as an isopropenyl group, an (E)-1-methyl-1-propenyl group, a (Z)-1-methyl-1-propenyl group, a 2-methyl-1-propenyl group, and an isopentenyl group; cyclic alkenyl groups such as a 2-cyclohexenyl group; aryl groups such as a phenyl group, an o-tolyl group, a m-tolyl group, and a p-tolyl group; aralkyl groups such as a benzyl group; and isomers thereof. A part of the hydrogen atoms in the hydrocarbon groups may be substituted with a methyl or ethyl group.

A particularly preferred example is a sec-butyl group, wherein the sec-butyl group and the carbonyloxy group to which the sec-butyl group is bonded form together a 2-methylbutyrate compound. The esterified product constitutes the naturally occurring pheromone of ARMB. In this case, the ester compound includes (R)-2-methylbutyrate, (S)-2-methylbutyrate, and a mixture thereof in any ratio.

Specific examples of 2-(1,2,2-trimethyl-3-cyclopentenyl)-2-oxoethyl carboxylate compound (6) include the following compounds.

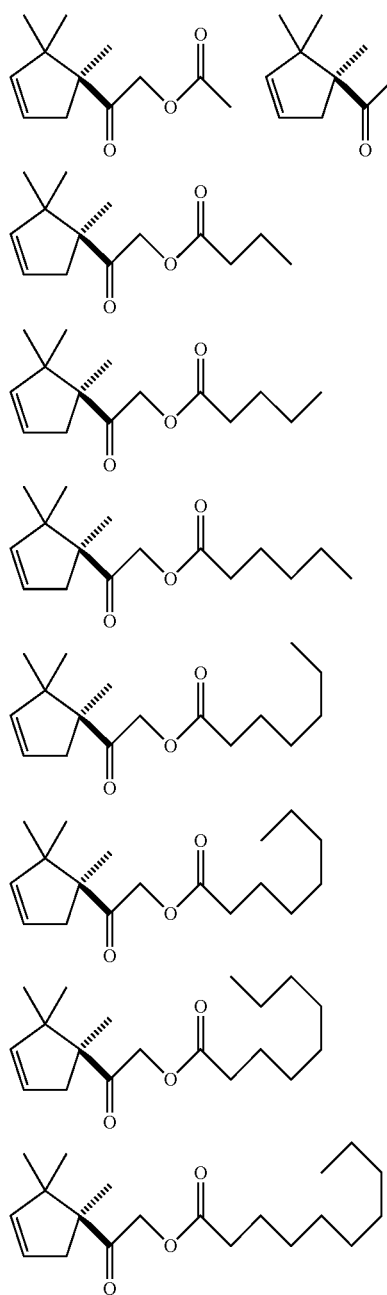

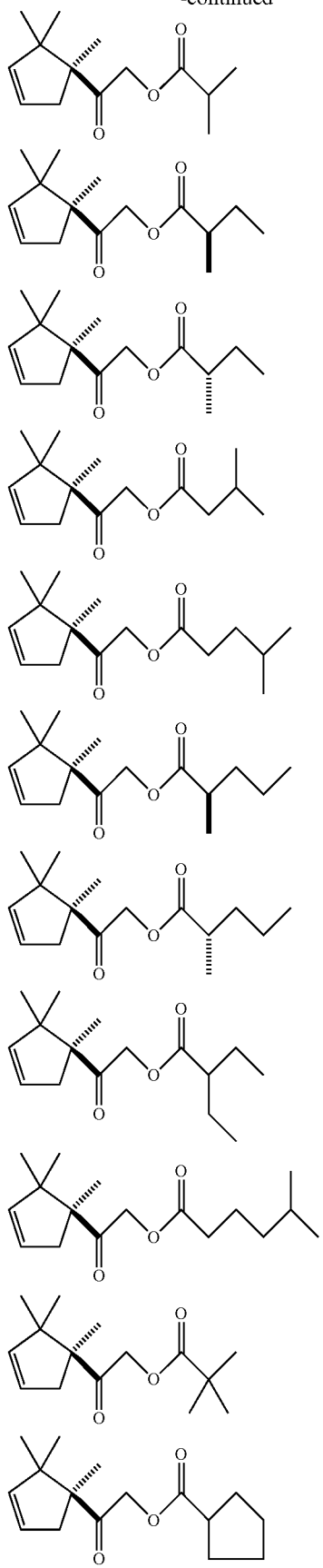

-continued

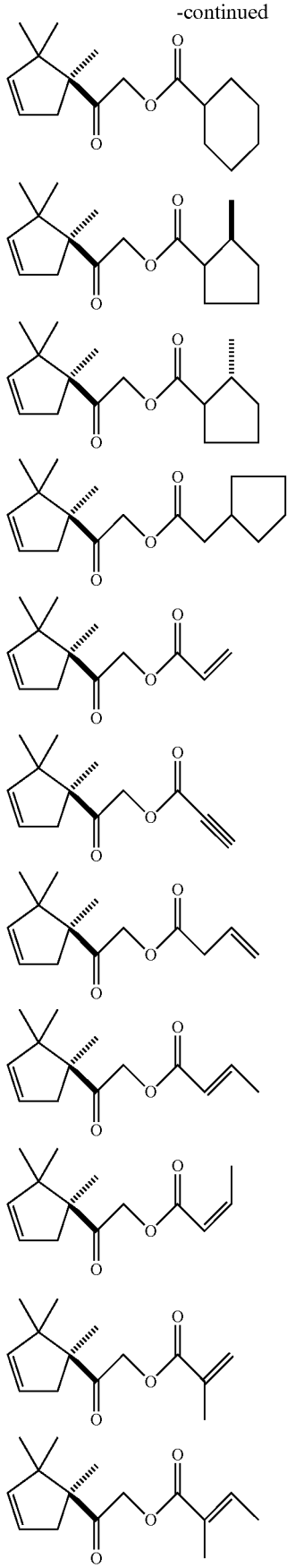
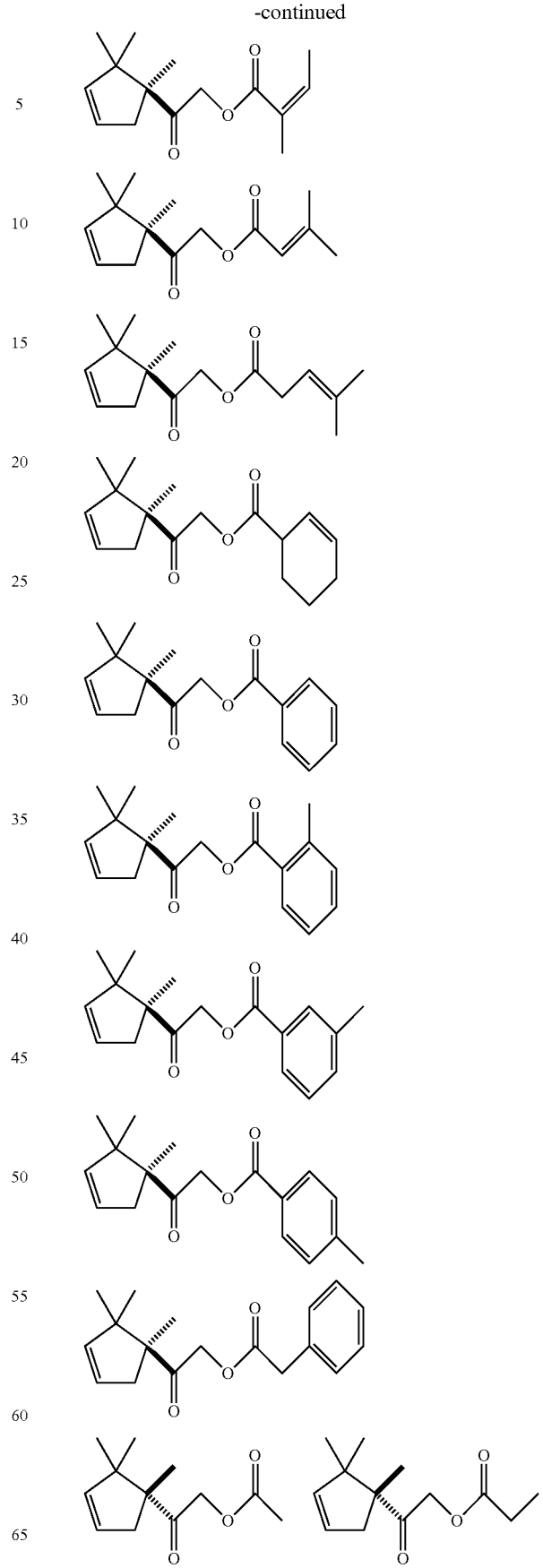

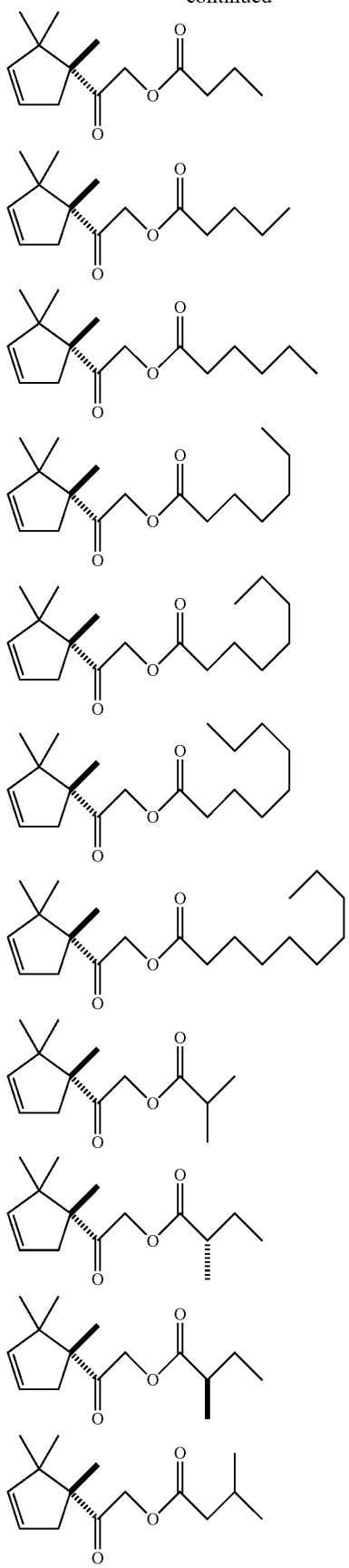
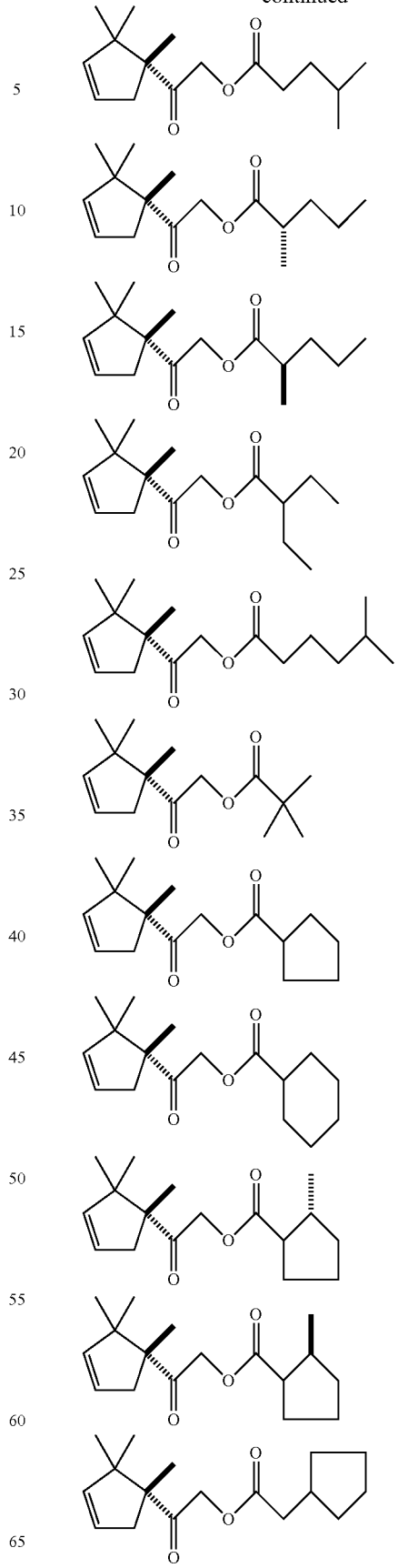

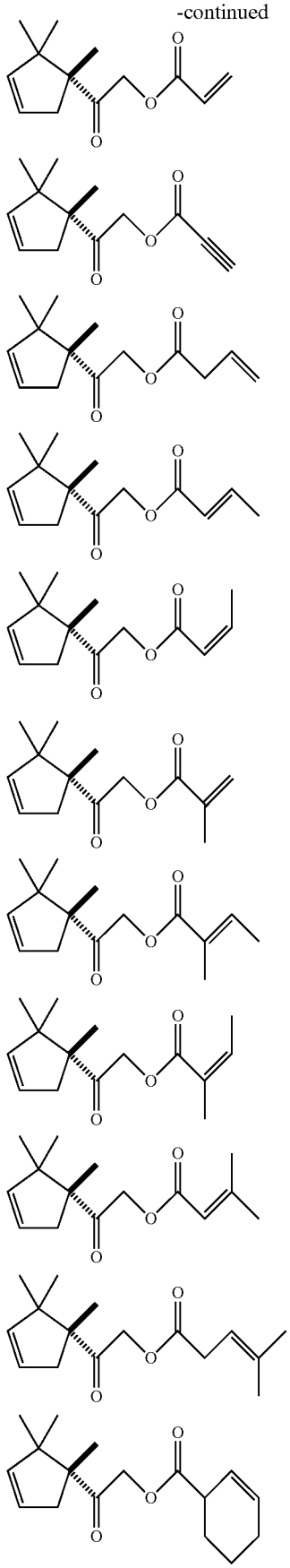
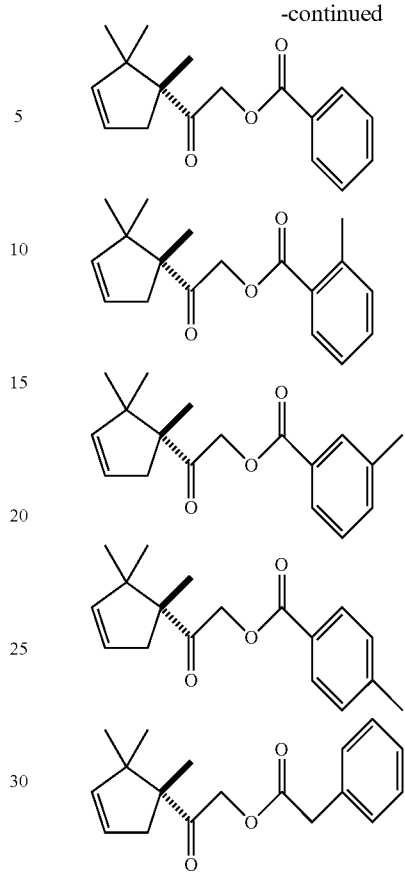

The esterification reaction may be done in any known process for preparing an ester. Examples of the esterification reaction include (I) esterification reaction with a carboxylic acid compound, (II) esterification reaction with an acylating agent, (III) esterification reaction with a carboxylate salt, and (IV) esterification reaction with an alkyl carboxylate compound.

In method (I) of esterification with a carboxylic acid compound, hydroxymethyl 1,2,2-trimethyl-3-cyclopentenyl ketone (3) and/or halomethyl 1,2,2-trimethyl-3-cyclopentenyl ketone compound (7) reacts with a carboxylic acid compound to form the 2-(1,2,2-trimethyl-3-cyclopentenyl)-2-oxoethyl carboxylate compound (6), as shown in the following chemical reaction formulae.

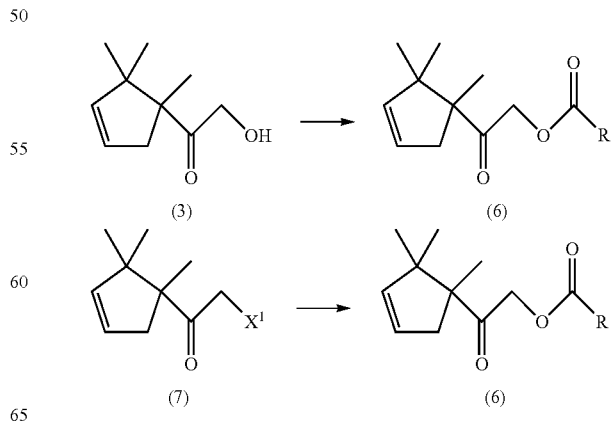

wherein R and $X^1$ are as defined above.

The carboxylic acid compound is represented by the following general formula (8):

(8)

wherein R is as defined above.

R in carboxylic acid compound (8) is the same as the monovalent hydrocarbon group described above.

Examples of the carboxylic acid compound (8) include saturated linear carboxylic acids such as acetic acid, propionic acid, butyric acid, valeric acid, hexanoic acid, heptanoic acid, octanoic acid, nonanoic acid, and decanoic acid; saturated branched carboxylic acids such as 2-methyl propionic acid (or isobutyric acid), (S)-2-methylbutanoic acid, (R)-2-methylbutanoic acid, 3-methylbutanoic acid (or isovaleric acid), 4-methylpentanoic acid, (S)-2-methylpentanoic acid, (R)-2-methylpentanoic acid, 2-ethylbutanoic acid, 5-methylhexanoic acid, and pivalic acid; saturated cyclic carboxylic acids such as cyclopentanecarboxylic acid, cyclohexanecarboxylic acid, 2-methylcyclopentanecarboxylic acid, and cyclopentane acetic acid; unsaturated linear carboxylic acids such as acrylic acid, propiolic acid, 3-butenoic acid, crotonic acid, and isocrotonic acid; unsaturated branched carboxylic acids such as methacrylic acid, tiglic acid, angelic acid, senecioic acid, and 4-methyl-4-pentene acid; unsaturated cyclic carboxylic acids such as 2-cyclohexenecarboxylic acid; and aromatic carboxylic acids such as benzoic acid, o-toluic acid, m-toluic acid, p-toluic acid, and phenylacetic acid.

A particularly preferred example is 2-methylbutanoic acid, which is esterified to form the naturally occurring pheromone compound. This carboxylic acid compound includes (S)-2-methylbutanoic acid, (R)-2-methylbutanoic acid, and a mixture thereof in any ratio.

The carboxylic acid compound (8) may be used either alone or in combination thereof, if necessary. The carboxylic acid compound (8) may be commercially available one.

An amount of the carboxylic acid compound (8) is preferably from 1 to 500 mol, more preferably 1 to 50 mol, and even more preferably 1 to 5 mol, per mol of the hydroxymethyl 1,2,2-trimethyl-3-cyclopentenyl ketone (3) and/or halomethyl 1,2,2-trimethyl-3-cyclopentenyl ketone (7).

A solvent may be used in the esterification reaction with the carboxylic acid compound (8).

Examples of the solvent include haloalkanes such as methylene chloride, chloroform, and trichloroethylene; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, and 1,4-dioxan; nitriles such as acetonitrile; ketones such as acetone and 2-butanone; esters such as ethyl acetate and n-butyl acetate; polar aprotic solvents such as N,N-dimethylformamide, dimethyl sulfoxide, and hexamethyl phosphoric triamide; and water.

The solvent may be used either alone or in combination thereof, if necessary. The solvent may be commercially available one.

An amount of the solvent is preferably from 100 to 1,000,000 mL per mol of the hydroxymethyl 1,2,2-trimethyl-3-cyclopentenyl ketone (3) and/or the halomethyl 1,2,2-trimethyl-3-cyclopentenyl ketone (7).

An acid catalyst may be used in the esterification reaction with carboxylic acid compound (8). The esterification reaction in this case is a dehydration reaction between hydroxymethyl 1,2,2-trimethyl-3-cyclopentenyl ketone (3), which is a preferred reactive substrate, and the carboxylic acid compound (8).

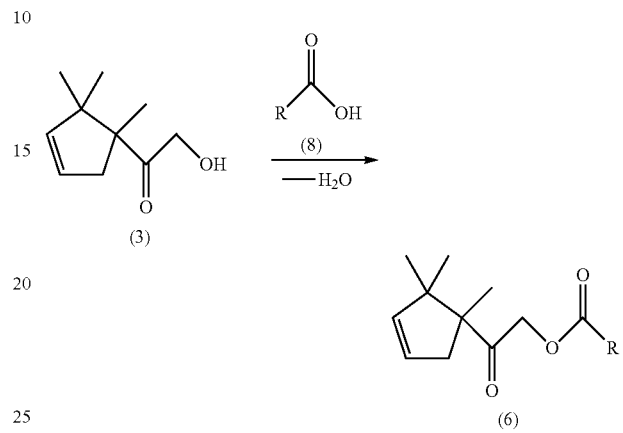

wherein R is as defined above.

Examples of the acid catalyst include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide; and acidic ion exchange resins.

The acid catalyst may be used either alone or in combination thereof, if necessary. The acid catalyst may be commercially available one.

An amount of the acid catalyst used is preferably from 0.0001 to 100 mol, more preferably 0.001 to 1 mol, and even more preferably 0.01 to 0.05 mol, per mol of the hydroxymethyl 1,2,2-trimethyl-3-cyclopentenyl ketone (3) and/or the halomethyl 1,2,2-trimethyl-3-cyclopentenyl ketone (7).

A base may be in the esterification reaction with the carboxylic acid compound (8). The esterification reaction in this case is a dehydrohalogenation between the halomethyl 1,2,2-trimethyl-3-cyclopentenyl ketone compound (7), which is a preferred reactive substrate, and the carboxylic acid compound (8).

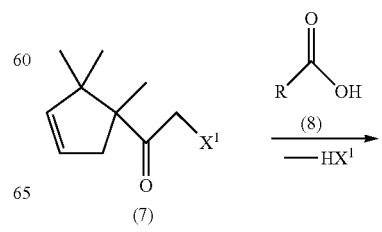

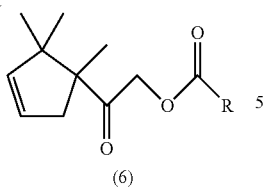

(6)

Examples of the base includes inorganic bases including hydroxides such as lithium hydroxide, sodium hydroxide, potassium hydroxide, and barium hydroxide and carbonates such as potassium carbonate; organic bases such as triethylamine, diisopropylethylamine, N,N-dimethylaniline, N,N-diethylaniline, pyridine, 2-ethylpyridine, and 4-dimethylaminopyridine; and basic ion exchange resins.

The base may be used either alone or in combination thereof, if necessary. The base may be commercially available one.

An amount of the base is preferably from 1 to 500 mol per mol of the hydroxymethyl 1,2,2-trimethyl-3-cyclopentenyl ketone (3) and/or the halomethyl 1,2,2-trimethyl-3-cyclopentenyl ketone (7).

A reaction temperature in the esterification reaction with carboxylic acid compound (8) may be selected, depending on reaction conditions. The reaction temperature is preferably from −50° C. to a boiling point of a solvent or 250° C., more preferably from 0° C. to a boiling point of a solvent, and even more preferably from 10° C. to a boiling point of a solvent.

The esterification reaction between hydroxymethyl 1,2,2-trimethyl-3-cyclopentenyl ketone (3) and the carboxylic acid compound (8) may be done in a solvent such as a hydrocarbon, such as hexane, heptane, benzene, toluene, xylene, and cumene, while removing the resulting water out of the system by azeotropic distillation. Alternatively, water may be distilled off with refluxing at the boiling point of the solvent at normal pressure, or distilled off at a lower temperature than the boiling point of water at a reduced pressure.

A reaction time of the esterification reaction with the carboxylic acid compound (8) is preferably from 5 minutes to 240 hours.

Method (II) of esterification with an acylating agent compound comprises an esterification reaction of hydroxymethyl 1,2,2-trimethyl-3-cyclopentenyl ketone (3) with an acylating agent compound to form the 2-(1,2,2-trimethyl-3-cyclopentenyl)-2-oxoethyl carboxylate compound (6).

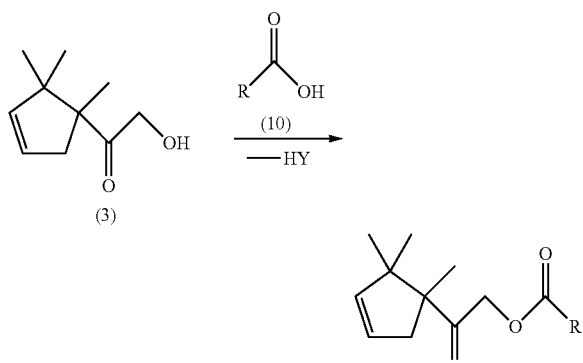

wherein R is as defined above, and Y represents a leaving group.

The acylating agent compound is represented by the following general formula (10):

(10)

wherein R is as defined above, and Y represents a leaving group.

Specific examples of R in the acylating agent compound (10) are same as those of the monovalent hydrocarbon group described above.

Examples of the acyl group, R—C(=O)—, in the acylating agent compound (10) include the acyl group in the carboxylic acid compound (8) used in the esterification reaction (I) with a carboxylic acid.

Examples of the acylating agent compound (10) include acyl halide (wherein Y is a halogen atom); carboxylic anhydride (wherein Y is an acyloxy group that may be the same as or different from RC(=O)—O—); carboxylic mixed anhydrides such as carboxylic/trifluoroacetic mixed anhydride (wherein Y is a trifluoroacetyloxy group), carboxylic/methanesulfonic mixed anhydride (wherein Y is a methanesulfonyloxy group), carboxylic/trifluoromethanesulfonic mixed anhydride (wherein Y is a trifluoromethanesulfonyloxy group), carboxylic/benzenesulfonic mixed anhydride (wherein Y is a benzenesulfonyloxy group), and carboxylic/p-toluenesulfonic mixed anhydride (wherein Y is a p-toluenesulfonyloxy group); and activated esters such as acyl imidazole (wherein Y is an imidazole residue), p-nitrophenyl carboxylate (wherein Y is a p-nitrophenyloxy group), pentafluorophenyl carboxylate (wherein Y is a pentafluorophenyl oxy group), 2,4,5-trichlorophenyl carboxylate (wherein Y is a 2,4,5-trichlorophenyl oxy group), N-acyloxy-5-norbornene-endo-2,3-dicarboxyimide (wherein Y is a 5-norbornene-endo-2,3-dicarboxyimide-N-oxy group), acyloxybenzotriazole (wherein Y is a benzotriazoloxy group), 1-acyloxy-7-azabenzotriazole (wherein Y is a 7-azabenzotriazoleoxy group), and N-acyloxysuccinimide (wherein Y is an N-hydroxysuccinimide-N-oxy group).

The acylating agent compound (10) may be used either alone or in combination thereof, if necessary. The acylating agent compound (10) may be commercially available one.

Examples of the acyl halide include acyl fluoride (wherein Y is a fluorine atom), acyl chloride (wherein Y is a chlorine atom), acyl bromide (wherein Y is a bromine atom), and acyl iodide (wherein Y is an iodine atom). Acyl chloride and acyl bromide are particularly preferred in view of their availability, and the reactivity and stability of intermediates from them.

A symmetrical acid anhydride having the same acyl group to be introduced (wherein Y is RC(=O)—O—) is preferable as a carboxylic anhydride, because an unnecessary by-product to be removed does not generate.

In a case where a carboxylic acid as a source for an acyl group to be introduced is expensive, a left carboxylic acid derived from the leaving group may be recovered. However, preferred is use of a mixed anhydride with another acid which is more easily left (i.e., which has a higher acidity). Examples of the mixed anhydride include mixed carboxylic anhydrides such as carboxylic/trifluoroacetic mixed anhydride, carboxylic/methanesulfonic mixed anhydride, carboxylic/trifluoromethanesulfonic mixed anhydride, carboxylic/benzenesulfonic mixed anhydride, and carboxylic/p-toluenesulfonic mixed anhydride.

An amount of the acylating agent compound (10) is preferably from 1 to 500 mol, more preferably from 1 to 50 mol, and even more preferably from 1 to 5 mol, per mol of hydroxymethyl 1,2,2-trimethyl-3-cyclopentenyl ketone (3).

A base may be used in the esterification reaction with the acylating agent compound (10).

Examples of the base includes inorganic bases including hydroxides such as lithium hydroxide, sodium hydroxide, potassium hydroxide, and barium hydroxide and carbonates such as potassium carbonate; organic bases such as triethylamine, diisopropylethylamine, N,N-dimethylaniline, N,N-diethylaniline, pyridine, 2-ethylpyridine, and 4-dimethylaminopyridine; and basic ion exchange resins.

The base may be used either alone or in combination thereof, if necessary. The base may be commercially available one.

An amount of the base is preferably from 1 to 500 mol per mol of the hydroxymethyl 1,2,2-trimethyl-3-cyclopentenyl ketone (3).

A solvent may be used in the esterification reaction with the acylating agent compound (10).

Examples of the solvent include haloalkanes such as methylene chloride, chloroform, and trichloroethylene; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, and 1,4-dioxan; nitriles such as acetonitrile; ketones such as acetone and 2-butanone; esters such as ethyl acetate and n-butyl acetate; polar aprotic solvents such as N,N-dimethylformamide, dimethyl sulfoxide, and hexamethyl phosphoric triamide; and water.

The solvent may be used either alone or in combination thereof, if necessary. The solvent may be commercially available one. When the base is in a liquid form, the base may work also as a solvent. When the base is in a solid form such as lithium hydroxide, the base may be dissolved in water in use.

An amount of the solvent is preferably from 100 to 1,000,000 mL per mol of hydroxymethyl 1,2,2-trimethyl-3-cyclopentenyl ketone (3).

An acid catalyst may be used in the esterification reaction with the acylating agent compound (10) such as a carboxylic anhydride, mixed carboxylic anhydride, p-nitrophenyl carboxylate, or carboxylic acid imidazolide.

Examples of the acid catalyst include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium (IV) oxide; and acidic ion exchange resins.

An amount of the acid catalyst used in an esterification reaction with an acylating agent compound such as a carboxylic anhydride, mixed carboxylic anhydride, or p-nitrophenyl carboxylate is preferably from 0.0001 to 100 mol per mol of the hydroxymethyl 1,2,2-trimethyl-3-cyclopentenyl ketone (3).

A reaction temperature in the esterification reaction with the acylating agent compound (10) may be selected, depending on the acylating agent and reaction conditions to be used. The reaction temperature is preferably from −50° C. to a boiling point of a solvent or 250° C., and more preferably from −20 to 150° C.

A reaction time in the esterification reaction with the acylating agent compound (10) is preferably from 5 minutes to 240 hours.

Method (III) of esterification reaction with a carboxylate salt compound comprises an esterification reaction of the halomethyl 1,2,2-trimethyl-3-cyclopentenyl ketone compound (7) with a carboxylate salt compound to form the 2-(1,2,2-trimethyl-3-cyclopentenyl)-2-oxoethyl carboxylate compound.

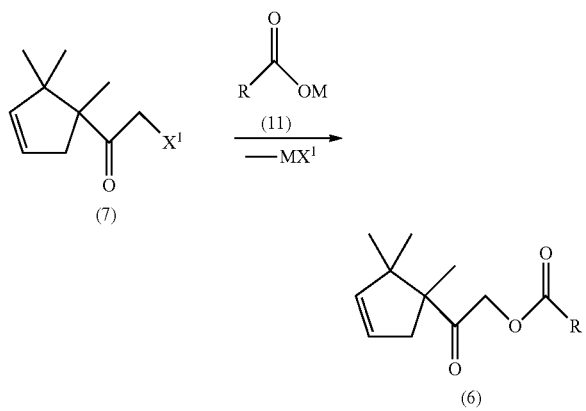

wherein X and R are as defined above, and M represents a metal atom.

The carboxylate salt compound is represented by the following general formula (11):

Specific examples of R in the carboxylate salt compound (11) are the same as those of the monovalent hydrocarbon group described above.

Examples of the carboxylate salt compound (11) include a salt of the carboxylic acid compound (8) used in the esterification reaction (I) with a carboxylic acid compound.

M in the carboxylate salt compound (11) represents a metal atom.

The carboxylate salt compound (11) is preferably alkaline metal salts such as lithium salt (wherein M is Li), sodium salt (wherein M is Na), and potassium salt (wherein M is K); and alkaline earth metal salts such as magnesium salt (wherein M is $Mg_{1/2}$), calcium salt (wherein M is $Ca_{1/2}$), and barium salt (wherein M is $Ba_{1/2}$).

The carboxylate salt compound (11) may be used either alone or in combination thereof, if necessary. The carboxylate salt compound (11) may be commercially available one.

The carboxylate salt compound (11) may be formed in situ in a reaction system by reacting the carboxylic acid compound (8) with the base described above.

An amount of the carboxylate salt compound (11) is preferably from 1 to 500 mol, more preferably 1 to 50 mol, and even more preferably 1 to 5 mol, per mol of the halomethyl 1,2,2-trimethyl-3-cyclopentenyl ketone compound (7).

Examples of a solvent used in the esterification reaction with carboxylate salt compound (11) include haloalkanes such as methylene chloride, chloroform, and trichloroethylene; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, and 1,4-dioxan; nitriles such as acetonitrile; ketones such as acetone and 2-butanone; esters such as ethyl acetate and n-butyl acetate; polar aprotic solvents such as N,N-dimethylformamide, dimethyl sulfoxide, and hexamethyl phosphoric triamide; and water.

The solvent may be used either alone or in combination thereof, if necessary. The solvent may be commercially available one.

An amount of the solvent is preferably from 100 to 1,000,000 mL per mol of the hydroxymethyl 1,2,2-trimethyl-3-cyclopentenyl ketone (3) and/or the halomethyl 1,2,2-trimethyl-3-cyclopentenyl ketone compound (7).

A reaction temperature in the esterification reaction with the carboxylate salt compound (11) may be selected, depending upon the carboxylate salt and reaction conditions to be used. The reaction temperature is preferably from −50° C. to a boiling point of a solvent or 250° C., and more preferably −20 to 150° C.

A reaction time of the esterification reaction with the carboxylate salt compound (11) is preferably from 5 minutes to 240 hours.

Method (IV) of esterification reaction with an alkyl carboxylate compound comprises an esterification reaction of hydroxymethyl 1,2,2-trimethyl-3-cyclopentenyl ketone (3) with an alkyl carboxylate compound to form the 2-(1,2,2-trimethyl-3-cyclopentenyl)-2-oxoethyl carboxylate compound (6),

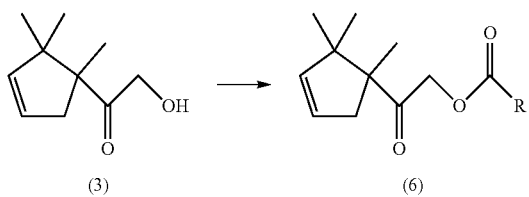

wherein R is as defined above.

The alkyl carboxylate compound is represented by the following general formula (12):

wherein R is as defined above, and Z represents a monovalent hydrocarbon group having 1 to 3 carbon atoms.

Specific examples of R in the alkyl carboxylate compound (12) are the same as those of the monovalent hydrocarbon group R described above.

Z in the alkyl carboxylate compound (12) represents a monovalent hydrocarbon group having 1 to 3 carbon atoms.

Examples of the monovalent hydrocarbon group having 1 to 3 carbon atoms include linear alkyl groups such as a methyl group, an ethyl group, and an n-propyl group; and branched alkyl groups such as an isopropyl group.

The esterification reaction with alkyl carboxylate compound (12) is preferably a transesterification wherein hydroxymethyl 1,2,2-trimethyl-3-cyclopentenyl ketone is reacted with an alkyl carboxylate compound having an envisaged monovalent hydrocarbon group R in the presence of a catalyst, and the resulting alcohol is removed.

The alkyl carboxylate compound (12) is preferably a primary alkyl ester of a carboxylic acid. Particularly preferred are methyl carboxylate, ethyl carboxylate, and n-propyl carboxylate in view of the price or ease of reaction progress.

Specific examples of the carboxylic acid which form a moiety of the alkyl carboxylate compound (12) are the same as those of the carboxylic acid compound (8) used in the esterification reaction with a carboxylic acid.

The alkyl carboxylate compound (12) may be used either alone or in combination thereof, if necessary. Alkyl carboxylate compound (12) may be commercially available one.

An amount of the alkyl carboxylate compound (12) is preferably from 1 to 500 mol, more preferably 1 to 50 mol, and even more preferably 1 to 5 mol, per mol of the hydroxymethyl 1,2,2-trimethyl-3-cyclopentenyl ketone (3).

Examples of the catalyst include acid catalysts, Lewis acid catalysts, base catalysts, and inorganic salt catalysts.

Examples of the acid catalyst include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and acidic ion exchange resins.

Examples of the Lewis acid catalyst include aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium (IV) oxide.

Examples of the base catalyst include bases such as sodium methoxide, sodium ethoxide, potassium t-butoxide, and 4-dimethylaminopyridine; and basic ion exchange resins.

Examples of the inorganic salt catalyst include salts such as sodium cyanide, potassium cyanide, sodium acetate, potassium acetate, calcium acetate, tin acetate, aluminum acetate, aluminum acetoacetate, and alumina.

The catalyst may be used either alone or in combination thereof, if necessary. The catalyst may be commercially available one.

An amount of the catalyst is preferably from 0.0001 to 100 mol, more preferably 0.001 to 1 mol, and even more preferably 0.01 to 0.05 mol, per mol of the hydroxymethyl 1,2,2-trimethyl-3-cyclopentenyl ketone (3).

The esterification reaction with alkyl carboxylate compound (12) may be carried out without any solvent (alternatively, the alkyl carboxylate compound itself, which is the reactant, may work as a solvent). This solvent-free reaction system is preferred, which makes extra operations such as concentration or solvent recovery, unnecessary.

A solvent may be used, if necessary.

Examples of the solvent include hydrocarbons such as hexane, heptane, benzene, toluene, xylene, and cumene; and ethers such as diethyl ether, dibutyl ether, diethyleneglycol diethyl ether, diethyleneglycol dimethyl ether, tetrahydrofuran, and 1,4-dioxane.

The solvent may be used in combination thereof, if necessary. The solvent may be commercially available one.

An amount of the solvent is preferably from 10 to 1,000,000 mL per mol of the hydroxymethyl 1,2,2-trimethyl-3-cyclopentenyl ketone (3).

A reaction temperature in the esterification reaction with the alkyl carboxylate compound (12) may be selected, depending upon an alkyl carboxylate compound and reaction conditions to be used. The esterification reaction is typically carried out under heating around a boiling point of a lower alcohol which generates in the transesterification and has 1 to 3 carbon atoms, that is, methanol, ethanol, 1-propanol, and 2-propano, while distillating the formed low-boiling alcohol off.

The alcohol may be distilled off at a lower temperature than its boiling point at a reduced pressure.

A reaction time of the esterification reaction with alkyl carboxylate compound (12) is preferably from 5 minutes to 240 hours.

2-(1,2,2-Trimethyl-3-cyclopentenyl)-2-oxoethyl carboxylate compound (6) thus prepared may be purified in any conventional purification method used in ordinary organic synthesis such as distillation or various chromatography.

Similarly as described on 2-(1,2,2-trimethyl-3-cyclopentenyl)-2-oxoethyl compound (5), halomethyl 1,2,2-trimethyl-3-cyclopentenyl ketone (7) is a stable synthetic intermediate. Therefore, the esterification reaction of halomethyl 1,2,2-trimethyl-3-cyclopentenyl ketone (7) with a carboxylic acid is particularly preferred for industrial preparation of a pheromone of ARMB and analogues thereof.

EXAMPLES

The present invention will be further described with reference to the following Examples. It should be noted that the present invention is not limited to or by the Examples. Preparation of the Pheromone Compounds of the ARMB and Analogues Thereof In the Examples, purities of raw materials, products, and intermediates were determined by gas chromatography (GC), and expressed as % GC. An isomer ratio of products or intermediates is a relative ratio of area percentages determined by GC.

GC conditions: GC: Shimadzu GC-14A, column: 5% Ph-Me silicone 0.25 mm$\phi$×25 m, carrier gas: He, detector: FID or Hewlett-Packard 7890B, column: 5% Ph-Me silicone 0.25 mm$\phi$×30 m, carrier gas: He, detector: FID.

Yield is calculated, based on % GC. Because the raw materials used in reactions and the products obtained in reactions did not always have a purity of 1000, a yield is calculated by the following equation:

Yield (%)={[(mass of a product obtained in a reaction×% GC)/molecular mass of a product]+[(mass of a raw material×% GC)/molecular mass of a raw material]}×100

Detection sensitivities in gas chromatography may differ among compounds, so that yields may sometimes exceed 100%, particularly when a raw material or a product is crude.

Crude products were purified to obtain sample compounds for observing spectra or samples to be used in bioactivity tests, where necessary.

Example 1

(S)-Bromomethyl 1,2,2-trimethyl-3-cyclopentenyl ketone (7: (S)-(7), X$^1$=Br) was prepared in Example 1-1 and Example 1-2 below.

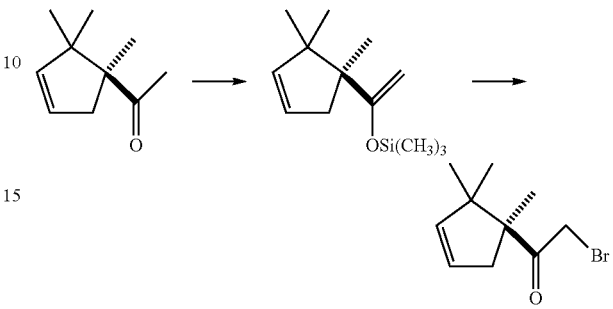

Example 1-1: Synthesis of (S)-1,2,2-trimethyl-1-(1-trimethylsilyloxyvinyl)-3-cyclopentene

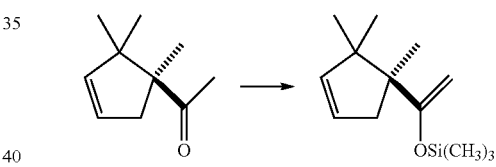

To a mixture of a solution of (S)-methyl 1,2,2-trimethyl-3-cyclopentenyl ketone (9) [100% ee, [α]$_D^{24}$−149° (c=1.02, CHCl$_3$)] in diethyl ether (13.13 g, 46.2% GC), diisopropylethylamine (12.93 g), and dichloromethane (60 mL) was added dropwise a mixture of trimethylsilyl trifluoromethanesulfonyl (14.0 g) and dichloromethane (20 mL) in a nitrogen atmosphere at 10° C. or lower, while stirred and cooled in an ice-water bath. After the completion of the dropwise addition, the reaction mixture was stirred, while cooled with ice, for 2 hours, and at room temperature for 14 hours. Then, the reaction mixture was poured into a saturated aqueous solution of sodium bicarbonate and extracted with n-hexane. The organic layer was subjected to ordinary post-treatments, i.e., washing, drying, and concentration, to obtain crude (S)-1,2,2-trimethyl-1-(1-trimethylsilyloxyvinyl)-3-cyclopentene in n-hexane (14.78 g, 29.0% GC, yield 48%). This was used as such in a liquid state in a subsequent reaction.

(S)-1,2,2-Trimethyl-1-(1-trimethylsilyloxyvinyl)-3-cyclopentene

GC-MS (EI, 70 eV): 45, 73, 91, 105, 119, 141, 168, 181, 195, 209 (base peak), 224 (M$^+$).

Example 1-2: Synthesis of (S)-bromomethyl 1,2,2-trimethyl-3-cyclopentenyl ketone (7: (S)-(7), $X^1$=Br)

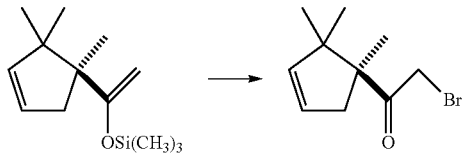

To a mixture of the crude (S)-1,2,2-trimethyl-1-(1-trimethylsilyloxyvinyl)-3-cyclopentene in n-hexane (14.78 g) obtained in Example 1-1, sodium bicarbonate (5.00 g), and tetrahydrofuran (150 mL) was added N-bromosuccinimide (10.0 g) in a nitrogen atmosphere at −60° C. or lower, while stirred and cooled in a dry ice-acetone bath. The reaction mixture was stirred at −60° C. or lower for 140 minutes. The cooling bath was then removed, and the temperature was gradually raised to 3° C. over 30 minutes. The reaction mixture was stirred, cooled with ice, further for 40 minutes. Saturated brine was added to quench the reaction and the mixture was subjected to extraction with n-hexane. The organic layer was subjected to ordinary post-treatments, i.e., washing, drying, and concentration. The concentrate was dissolved in dichloromethane and purified by silica gel column chromatography (eluent: n-hexane:diethylether=9:1) to obtain the target chemical compound, (S)-bromomethyl 1,2,2-trimethyl-3-cyclopentenyl ketone (7: (S)-(7), $X^1$=Br) in two fractions (5.62 g, 78% GC and 0.65 g, 62.8% GC) in a total yield of 109%.

(S)-Bromomethyl 1,2,2-trimethyl-3-cyclopentenyl ketone

Yellow oil.

IR (D-ATR): ν=3055, 2962, 2870, 1715, 1650, 1457, 1389, 1375, 1367, 1264, 1150, 1023, 832, 717 cm$^{-1}$.

$^1$H-NMR (500 MHz, CDCl$_3$): δ=0.87 (3H, s), 1.14 (3H, s), 1.23 (3H, s), 2.13 (1H, ddd, J=1.3, 2.7, 16.6 Hz), 3.15 (1H, dt-like, J=2.3, 16.4 Hz), 4.12 (1H, d, J=13.9 Hz), 4.17 (1H, d, J=13.8 Hz), 5.38 (1H, ddd, J=1.4, 2.5, 7.3 Hz), 5.60 (1H, dt-like, J=~2.4, 5.7 Hz) ppm.

$^{13}$C-NMR (125 MHz, CDCl$_3$): δ=21.61, 23.01, 24.82, 34.61, 41.77, 49.11, 60.02, 125.81, 139.78, 204.41 ppm.

GC-MS (EI, 70 eV): 43, 67, 79, 91, 109 (base peak), 123, 137, 151, 215, 230 (M$^+$).

The 78% GC fraction contained 6.5% GC of (S)-chloromethyl 1,2,2-trimethyl-3-cyclopentenyl ketone, which is represented by the following chemical formula and is a compound (S)-(7) wherein X is Cl. This compound is thought to have been formed on silica gel through halogen exchange with a chlorine source probably derived from dichloromethane used for chromatography.

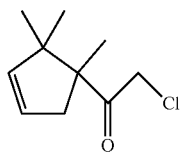

(S)-Chloromethyl 1,2,2-trimethyl-3-cyclopentenyl ketone

GC-MS (EI, 70 eV): 41, 67, 77, 91, 109 (base peak), 122, 137, 151, 171, 186 (M$^+$).

Example 2: Synthesis of (S)-2-(1,2,2-trimethyl-3-cyclopentenyl)-2-oxoethyl (S)-2-methylbutyrate (compound (6): (S,S)-(6), R=sec-butyl)

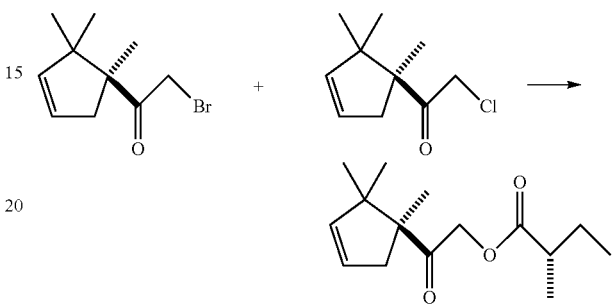

To a mixture of potassium carbonate (8.00 g) and N,N-dimethylformamide (40 mL) were added (S)-2-methylbutanoic acid (2.0 g, 98.6% ee, compound (8): (S)-8, R=sec-butyl), and then 2.50 g of the mixture, obtained in Example 1, of (S)-bromomethyl 1,2,2-trimethyl-3-cyclopentenyl ketone (78.0% GC) and (S)-chloromethyl 1,2,2-trimethyl-3-cyclopentenyl ketone (6.5% GC), while stirring at room temperature, and further stirred for 210 minutes in a nitrogen atmosphere. According to GC, both of the bromomethyl ketone compound and the chloromethyl ketone compound were converted into the target compound. The reaction mixture was then poured into ice water and subjected to extraction with n-hexane. The organic layer was subjected to ordinary post-treatments, i.e., washing, drying, and concentration. The concentrate was purified by silica gel column chromatography (eluent: n-hexane:diethylether=100:0 to 97:3) to obtain the target chemical compound, (S)-2-(1,2,2-trimethyl-3-cyclopentenyl)-2-oxoethyl (S)-2-methylbutyrate in two fractions (0.71 g, 93.1% GC and 1.20 g, 99.6% GC) in a total yield of 82%.

(S)-2-(1,2,2-Trimethyl-3-cyclopentenyl)-2-oxoethyl (S)-2-methylbutyrate

Yellowish oil.

[α]$_D^{24}$−65.0° (c=1.01, CHCl$_3$)

IR (D-ATR): ν=3056, 2969, 2937, 2877, 1744, 1718, 1461, 1414, 1261, 1178, 1151, 1015, 748, 717 cm$^1$.

$^1$H-NMR (500 MHz, C$_6$D$_6$, sample 20.2 mg/C$_6$D$_6$ 0.58 mL): δ=0.90 (3H, s), 0.94 (3H, s), 0.95 (3H, t, J=7.3 Hz), 0.95 (3H, s), 1.19 (3H, d, J=7.1 Hz), 1.40-1.50 (1H, ddq-like m), 1.70 (1H, dq-like, J=16.2, 1.3 Hz), 1.77-1.86 (1H, m), 2.42-2.49 (1H, dq-like m), 2.92 (1H, dt-like, J=16.3, 2.3 Hz), 4.53 (1H, d, J=16.7 Hz), 4.59 (1H, d, J=16.7 Hz), 5.10 (1H, dq-like, J=5.8, 1.3 Hz), 5.27-5.31 (1H, m) ppm.

In the $^1$H-NMR spectrum described above, minor peaks of methylene hydrogen atoms adjacent to the carbonyl group of a diastereomer (S)-2-(1,2,2-trimethyl-3-cyclopentenyl)-2-oxoethyl (R)-2-methylbutyrate were observed: δ=4.54 (1H, d, J=~16 Hz), 4.58 (1H, d, J=~16 Hz) ppm. According to a ratio of these peak areas, a ratio of the (S,S)-isomer to the (S,R)-isomer is about 99:1, which corresponds well to the optical purity of the starting material, (S)-2-methylbutanoic acid, within the NMR resolution.

In the $^1$H-NMR, concentration-dependent change of chemical shift, particularly, shift of the peak owing to the methyl groups, was observed. On a sample solution which was obtained by diluting 2 of the sample solution for the aforesaid spectrometry (20.2 mg/0.58 mL) with 0.56 mL of C$_6$D$_6$, peaks owing to the methyl groups are: δ=0.91 (3H, s), 0.94 (3H, s), 0.95 (3H, s), 0.97 (3H, t, J=7.4 Hz) ppm.

$^{13}$C-NMR (125 MHz, C$_6$D$_6$): δ=11.77, 16.97, 20.94, 22.69, 24.52, 27.15, 41.01, 41.15, 49.07, 58.49, 66.59, 125.78, 140.16, 175.51, 205.14 ppm.

GC-MS (EI, 70 eV): 41, 57, 85, 109 (base peak), 123, 137, 194, 209, 223, 237, 252 (M$^+$).

Example 3: Synthesis of (S)-2-(1,2,2-trimethyl-3-cyclopentenyl)-2-oxoethyl (R)-2-methylbutyrate (compound (6): (S,R)-(6), R=sec-butyl)

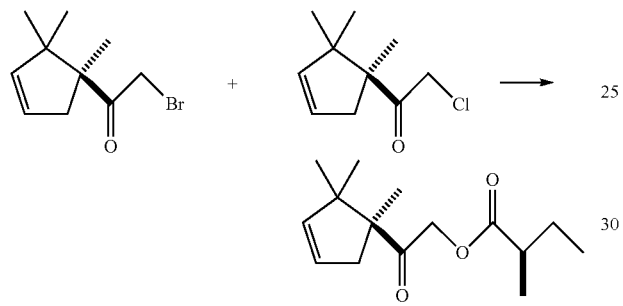

The procedures of Example 2 were repeated with the exception that 1.0 g of (R)-2-methylbutanoic acid (89.3% ee, compound (8): (R)-(8), R=sec-butyl) was used instead of 2.0 g of (S)-2-methylbutanoic acid (98.6% ee), and that the amount of the mixture of (S)-bromomethyl 1,2,2-trimethyl-3-cyclopentenyl ketone (78% GC) and (S)-chloromethyl 1,2,2-trimethyl-3-cyclopentenyl ketone (6.5% GC) was 1.0 g instead of 2.50 g, so that obtained was the target chemical compound, (S)-2-(1,2,2-trimethyl-3-cyclopentenyl)-2-oxoethyl (R)-2-methylbutyrate in two fractions (0.21 g, 87.6% GC and 0.62 g, 99.4% GC) in a total yield of 94%.

(S)-2-(1,2,2-Trimethyl-3-cyclopentenyl)-2-oxoethyl (R)-2-methylbutyrate

Yellowish oil.
$[α]_D^{24}$ −87.6° (c=1.01, CHCl$_3$)
IR (D-ATR): ν=3055, 2968, 2937, 2877, 1743, 1718, 1461, 1414, 1368, 1261, 1235, 1178, 1151, 1015, 748, 717 cm$^{-1}$.

$^1$H-NMR (500 MHz, C$_6$D$_6$, sample 19.8 mg/C$_6$D$_6$ 0.58 mL): δ=0.90 (3H, s), 0.94 (3H, s), 0.94 (3H, t, J=7.3 Hz), 0.95 (3H, s), 1.20 (3H, d, J=6.9 Hz), 1.40-1.50 (1H, ddq-like m), 1.70 (1H, dq-like, J=16.2, 1.3 Hz), 1.77-1.86 (1H, m), 2.42-2.48 (1H, dq-like m), 2.89-2.94 (1H, dt-like, J=16.5, 2.3 Hz), 4.54 (1H, d, J=16.7 Hz), 4.58 (1H, d, J=16.7 Hz), 5.11 (1H, dq-like, J=5.8, 1.3 Hz), 5.29 (1H, dt-like, J=5.7, 2.3 Hz) ppm.

In the $^1$H-NMR spectrum described above, minor peaks of the methylene hydrogen atoms adjacent to the carbonyl group of a diastereomer, (S)-2-(1,2,2-trimethyl-3-cyclopentenyl)-2-oxoethyl (S)-2-methylbutyrate, were observed: δ=4.53 (1H, d, J=16.7 Hz), 4.59 (1H, d, J=~16.7 Hz) ppm.

According to a ratio of these peak areas, a ratio of the (S,R)-isomer to the (S,S)-isomer is about 95:5, which corresponds well to the optical purity of the starting material, (R)-2-methylbutanoic acid, within the NMR resolution.

$^{13}$C-NMR (125 MHz, C$_6$D$_6$): δ=11.78, 17.02, 20.95, 22.69, 24.52, 27.12, 41.01, 41.18, 49.07, 58.49, 66.58, 125.78, 140.16, 175.50, 205.14 ppm.

GC-MS (EI, 70 eV): 41, 57, 85, 109 (base peak), 123, 137, 168, 194, 209, 223, 237, 252 (M).

Example 4

(R)-Bromomethyl 1,2,2-trimethyl-3-cyclopentenyl ketone (compound (R)-7, X=Br) was prepared in Example 4-1 and Example 4-2 below.

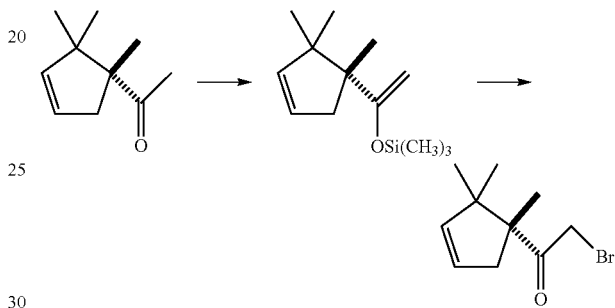

Example 4-1: Synthesis of (R)-1,2,2-trimethyl-1-(1-trimethylsilyloxyvinyl)-3-cyclopentene

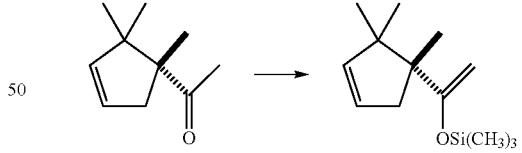

The procedures of Example 1-1 was repeated with the exception that 2.14 g of (R)-methyl 1,2,2-trimethyl-3-cyclopentenyl ketone [100% ee, $[α]_D^{23}$+149° (c=1.01, CHCl$_3$)] in diethyl ether (37.2% GC) was used instead of 13.13 g of (S)-methyl 1,2,2-trimethyl-3-cyclopentenyl ketone in diethyl ether (46.2% GC), so that obtained was crude (R)-1,2,2-trimethyl-1-(1-trimethylsilyloxyvinyl)-3-cyclopentene in n-hexane (2.29 g, 29.2% GC, yield 57%). This was used as such in a solution form in a subsequent reaction The resulting (R)-1,2,2-trimethyl-1-(1-trimethylsilyloxyvinyl)-3-cyclopentene has the same GC-MS spectrum as that of (S)-1,2,2-trimethyl-1-(1-trimethylsilyloxyvinyl)-3-cyclopentene obtained in Example 1-1.

Example 4-2: Synthesis of (R)-bromomethyl 1,2,2-trimethyl-3-cyclopentenyl ketone (7: (R)-(7), X¹=Br)

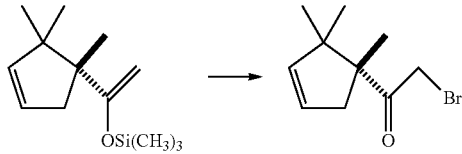

The procedures of Example 1-2 were repeated with the exception that 2.29 g of the solution of crude (R)-1,2,2-trimethyl-1-(1-trimethylsilyloxyvinyl)-3-cyclopentene in n-hexane (29.2% GC, 100% ee) obtained in Example 4-1 was used instead of the solution of crude (S)-1,2,2-trimethyl-1-(1-trimethylsilyloxyvinyl)-3-cyclopentene in n-hexane used in Example 1-2, so that obtained was the target chemical compound, (R)-bromomethyl 1,2,2-trimethyl-3-cyclopentenyl ketone (7: (R)-(7), X¹=Br) (1.86 g, 57.4% GC, yield 98%).

The IR, ¹H-NMR, ¹³C-NMR, and GC-MS spectra of (R)-bromomethyl 1,2,2-trimethyl-3-cyclopentenyl ketone (7: (R)-(7), X¹=Br)(yellowish oil) obtained above were identical to those of (S)-bromomethyl 1,2,2-trimethyl-3-cyclopentenyl ketone (7: (S)-(7), X¹=Br) obtained in Example 1-2.

Example 5: Synthesis of (R)-2-(1,2,2-trimethyl-3-cyclopentenyl)-2-oxoethyl (S)-2-methylbutyrate (compound (6): (R,S)-(6), R=sec-butyl)

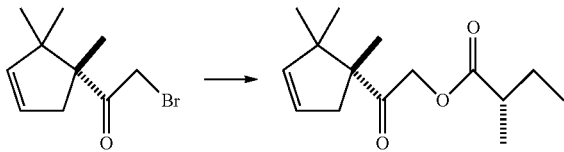 [SMILES: CC1(C)C=CC[C@@]1(C)C(=O)CBr ; CC[C@H](C)C(=O)OCC(=O)[C@]1(C)CC=CC1(C)C]

The procedures of Example 2 were repeated with the exception that 1.86 g of (R)-bromomethyl 1,2,2-trimethyl-3-cyclopentenyl ketone (57% GC, 100% ee) obtained in Example 4-2 was used instead of the mixture of (S)-bromomethyl 1,2,2-trimethyl-3-cyclopentenyl ketone (78% GC) and (S)-chloromethyl 1,2,2-trimethyl-3-cyclopentenyl ketone (6.5% GC) and that the amount of (S)-2-methylbutanoic acid (98.6% ee) was 1.10 g, so that obtained was the target chemical compound, (R)-2-(1,2,2-trimethyl-3-cyclopentenyl)-2-oxoethyl (S)-2-methylbutyrate (0.66 g, 95.8% GC, yield 54%).

(R)-2-(1,2,2-Trimethyl-3-cyclopentenyl)-2-oxoethyl (S)-2-methylbutyrate

Yellowish oil.
$[\alpha]_D^{24}$+78.0° (c=1.02, CHCl$_3$)
The IR, ¹H-NMR, ¹³C-NMR, and GC-MS spectra of this compound were identical to those of (S)-2-(1,2,2-trimethyl-3-cyclopentenyl)-2-oxoethyl (R)-2-methylbutyrate obtained in Example 3.

In the ¹H-NMR spectrum described above, peaks of the methylene hydrogen atoms adjacent to the carbonyl group of a diastereomer, (R)-2-(1,2,2-trimethyl-3-cyclopentenyl)-2-oxoethyl (R)-2-methylbutyrate were minor, which corresponds well to the optical purity of the starting material, (S)-2-methylbutanoic acid, within the NMR resolution.

Example 6: Synthesis of (R)-2-(1,2,2-trimethyl-3-cyclopentenyl)-2-oxoethyl (R)-2-methylbutyrate (compound (6): (R,R)-(6), R=sec-butyl)

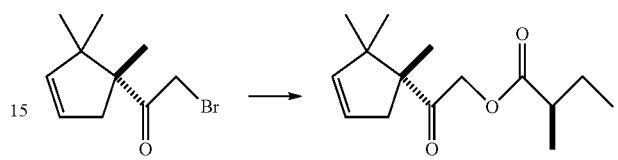

The procedures of Example 2 were repeated with the exception that 8.50 g of (R)-bromomethyl 1,2,2-trimethyl-3-cyclopentenyl ketone (48% GC, 100% ee) synthesized as in Example 4 was used instead of the mixture, used in Example 2, of (S)-bromomethyl 1,2,2-trimethyl-3-cyclopentenyl ketone (78% GC) and (S)-chloromethyl 1,2,2-trimethyl-3-cyclopentenyl ketone (6.5% GC), and that 5.00 g of (R)-2-methylbutanoic acid (89.3% ee) was used instead of (S)-2-methylbutanoic acid used in Example 2, so that obtained was the target chemical compound, (R)-2-(1,2,2-trimethyl-3-cyclopentenyl)-2-oxoethyl (R)-2-methylbutyrate in two fractions (2.18 g, 97.9% GC and 1.05 g, 99.1% GC) in a total yield of 74%.

(R)-2-(1,2,2-Trimethyl-3-cyclopentenyl)-2-oxoethyl (R)-2-methylbutyrate

Yellowish oil.
$[\alpha]_D^{24}$+66.2° (c=1.00, CHCl$_3$)
The IR, ¹H-NMR, ¹³C-NMR, and GC-MS spectra of this compound were identical to those of (S)-2-(1,2,2-trimethyl-3-cyclopentenyl)-2-oxoethyl (S)-2-methylbutyrate obtained in Example 2.

In the ¹H-NMR spectrum described above, minor peaks of the methylene hydrogen atoms adjacent to the carbonyl group of a diastereomer, (R)-2-(1,2,2-trimethyl-3-cyclopentenyl)-2-oxoethyl (S)-2-methylbutyrate were observed. According to a ratio of these peak areas, a ratio of the (R,R)-isomer to the (R,S)-isomer is (95.6-95.8): (4.4-4.2) in the two fractions, which corresponds well to the optical purity of the starting material, (R)-2-methylbutanoic acid, within the NMR resolution.

Example 7: Synthesis of (S)-2-(1,2,2-trimethyl-3-cyclopentenyl)-2-oxoethyl benzoate (Compound (6): (S)-(6), R=Ph)

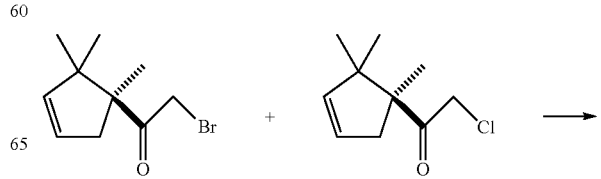

-continued

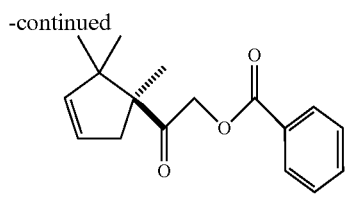

The procedures of Example 2 were repeated with the exception that 150 mg of benzoic acid (compound (8), R=phenyl) was used instead of (S)-2-methylbutanoic acid and that use was made of 100 mg of the mixture of (S)-bromomethyl 1,2,2-trimethyl-3-cyclopentenyl ketone (78% GC) and (S)-chloromethyl 1,2,2-trimethyl-3-cyclopentenyl ketone (6.5% GC) prepared as in Example 1, so that obtained was the target chemical compound, (S)-2-(1,2,2-trimethyl-3-cyclopentenyl)-2-oxoethyl benzoate (80 mg, 98.2% GC, 87% yield).

(S)-2-(1,2,2-Trimethyl-3-cyclopentenyl)-2-oxoethyl benzoate

Yellowish oil.
$[\alpha]_D^{24}$ −55.5° (c=1.00, CDCl$_3$)
IR (D-ATR): ν=3059, 2962, 2935, 2871, 1731, 1716, 1602, 1585, 1452, 1414, 1367, 1315, 1277, 1217, 1177, 1125, 1093, 1025, 748, 709 cm$^{-1}$.
$^1$H-NMR (500 MHz, CDCl$_3$: δ=0.99 (3H, s), 1.19 (3H, s), 1.26 (3H, s), 2.11-2.16 (1H, dq-like, J=16.4, 1.4 Hz), 3.12-3.17 (1H, dt-like, J=16.4, 2.3 Hz), 5.05 (1H, d, J=16.8 Hz), 5.11 (1H, d, J=16.8 Hz), 5.42-5.44 (1H, dq-like, J=5.8, 1.4 Hz), 5.59 (1H, dt-like, J=2.3, 5.7 Hz), 7.42-7.46 (2H, m), 7.55-7.59 (1H, m), 8.09-8.11 (2H, m) ppm.
$^{13}$C-NMR (125 MHz, C$_6$D$_6$): δ=20.97, 22.88, 24.40, 40.93, 49.18, 58.65, 67.27, 125.69, 128.35, 129.49, 129.86, 133.19, 140.19, 166.00, 206.13 ppm.
GC-MS (EI, 70 eV): 41, 51, 67, 77, 91, 105, 109 (base peak), 135, 150, 164, 199, 214, 229, 272 (M$^+$).

Example 8: Synthesis of (S)-2-(1,2,2-trimethyl-3-cyclopentenyl)-2-oxoethyl valerate (Compound (6), R=n-butyl)

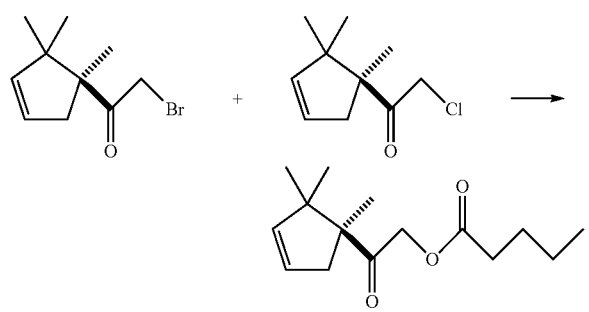

The procedures of Example 2 were repeated with the exception that 150 mg of valeric acid (compound (8), R=n-butyl) was used instead of (S)-2-methylbutanoic acid and that use was made of 150 mg of the mixture of (S)-bromomethyl 1,2,2-trimethyl-3-cyclopentenyl ketone (78% GC) and (S)-chloromethyl 1,2,2-trimethyl-3-cyclopentenyl ketone (6.5% GC) as prepared in Example 1, so that obtained was the target chemical compound, (S)-2-(1,2,2-trimethyl-3-cyclopentenyl)-2-oxoethyl valerate (110 mg, 96.8% GC, yield 77%).

(S)-2-(1,2,2-Trimethyl-3-cyclopentenyl)-2-oxoethyl valerate

Yellowish oil.
$[\alpha]_D^{23}$ −74.9° (c=1.00, CDCl$_3$)
IR (D-ATR): ν=3055, 2960, 2934, 2873, 1748, 1718, 1620, 1459, 1415, 1369, 1336, 1238, 1217, 1169, 1112, 1018, 991, 748, 717 cm$^{-1}$.
$^1$H-NMR (500 MHz, CDCl$_3$: δ=0.92 (3H, t, J=7.4 Hz), 0.99 (3H, s), 1.15 (3H, s), 1.20 (3H, s), 1.32-1.42 (2H, m), 1.62-1.69 (2H, m), 2.06-2.10 (1H, dq-like, J=5.8, 1.4 Hz), 2.43 (2H, t, J=7.5 Hz), 3.06-3.11 (1H, dt-like, J=16.2, 2.3 Hz), 4.79 (1H, d, J=16.9 Hz), 4.86 (1H, d, J=16.8 Hz), 5.38-5.40 (1H, dq-like, J=5.8, 1.4 Hz), 5.58-5.60 (1H, ddd-like, J=2.1, 2.7, 5.3 Hz), 7.42-7.46 (2H, m), 7.55-7.59 (1H, m), 8.09-8.11 (2H, m) ppm.
$^{13}$C-NMR (125 MHz, C$_6$D$_6$): δ=13.69, 20.90, 22.19, 22.86, 24.32, 26.88, 33.52, 40.92, 49.09, 58.58, 66.66, 125.66, 140.13, 173.18, 206.43 ppm.
GC-MS (EI, 70 eV): 41, 67, 85,109 (base peak), 123, 137, 153, 168, 194, 209, 223, 237, 252 (M$^+$).

Example 9: Synthesis 1 of (S)-hydroxymethyl 1,2,2-trimethyl-3-cyclopentenyl ketone (Compound (S)-(3))

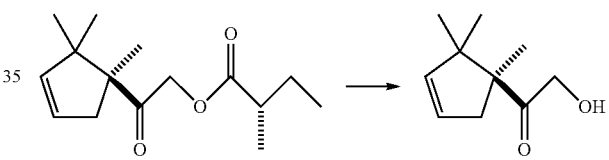

To a mixture of methanol (20 mL) and (S)-2-(1,2,2-trimethyl-3-cyclopentenyl)-2-oxoethyl (S)-2-methylbutyrate (100 mg, ~100% GC) synthesized. as in Example 2 and then purified by silica gel column chromatography was added 20 mg of a 28% by weight sodium methoxide solution in methanol in a nitrogen atmosphere. The reaction mixture was heated under reflux for 5 hours with stirring. The reaction mixture was cooled to room temperature, and was then neutralized and filtered by being let through 2.5 g of an acidic ion exchange resin, Amberlite FCP3500 which had been wetted with methanol and packed in a column. The reaction mixture was subjected to elution with methanol. The methanol-eluted fraction was concentrated at a reduced pressure to obtain the target chemical compound, (S)-hydroxymethyl 1,2,2-trimethyl-3-cyclopentenyl ketone (30 mg, yield 45%, gross). GC analysis failed to determine a purity of this compound due to partial thermal decomposition, but the NMR spectrum described below indicates that this compound is almost pure.

(S)-Hydroxymethyl 1,2,2-trimethyl-3-cyclopentenyl ketone

Yellowish oil.
$[\alpha]_D^{22}$ +131.6° (c=0.92, CDCl$_3$)
IR (D-ATR): ν=3468, 3055, 2963, 2934, 2872, 1700, 1621, 1459, 1403, 1367, 1337, 1278, 1217, 1108, 1081, 1022, 1012, 748, 717 cm$^{-1}$.

¹H-NMR (500 MHz, CDCl₃: δ=0.84 (3H, s), 1.15 (3H, s), 1.18 (3H, s), 2.04-2.09 (1H, dq-like, J=16.4, 1.4 Hz), 2.40-3.40 (1H, OH, br.), 3.06-3.10 (1H, dt-like, J=16.3, 2.3 Hz), 4.27 (1H, d, J=18.8 Hz), 4.37 (1H, d, J=18.8 Hz), 5.36-5.39 (1H, dq-like, J=5.7, 1.3 Hz), 5.60 (1H, ddd, J=2.1, 2.7, 5.8 Hz) ppm.
¹³C-NMR (125 MHz, C₆D₆): δ=21.00, 22.69, 24.56, 40.66, 49.40, 50.83, 66.75, 125.62, 139.70, 213.60 ppm.
GC-MS (EI, 70 eV): 41, 55, 67, 81, 91, 109 (base peak), 125, 137, 153, 168 (M⁺).
GC-MS (CI, isobutane): 75, 93, 109, 151, 169 [(M+1)⁺].
Substances caused by partial decomposition in GC were qualitatively analyzed with GC-MS. This revealed the presence of 2-(1,2,2-trimethyl-3-cyclopentenyl)-2-oxoacetaldehyde, which is a keto aldehyde compound having a formyl group resulting from oxidation of the hydroxymethyl group, and 1,2,2-trimethyl-3-cyclopentene-1-carboxylic acid, which is a carboxylic acid having a carboxyl group originated from the glycolyl group (HO—CH₂—C(=O)—).

2-(1,2,2-Trimethyl-3-cyclopentenyl)-2-oxoacetaldehyde

GC-MS (EI, 70 eV): 29, 41, 55, 67, 81, 91, 109 (base peak), 123, 137, 151, 165.
GC-MS (CI, isobutane): 71, 95, 121, 139 (base peak), 167 [(M+1)⁺].

1,2,2-Trimethyl-3-cyclopentene-1-carboxylic acid

GC-MS (CI, isobutane): 109, 155 [base peak, (M+1)⁺].

Reference Example 1: Synthesis 2 of (S)-hydroxymethyl 1,2,2-trimethyl-3-cyclopentenyl ketone (compound (S)-(3))

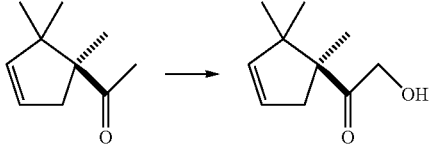

Bis(trifluoroacetoxy)iodobenzene (1.14 g) was added to a mixture of (S)-methyl 1,2,2-trimethyl-3-cyclopentenyl ketone (200 mg, 83% GC), acetonitrile (5 mL), water (1 mL), and trifluoroacetic acid (300 mg) at room temperature in a nitrogen atmosphere with stirring. The reaction mixture was heated under reflux for 3 hours with stirring. After cooled, the reaction mixture was diluted with diethyl ether and the reaction was quenched by adding a saturated aqueous solution of sodium bicarbonate. After ordinary extraction, washing, drying, and concentration, the concentrate was purified by silica gel column chromatography to obtain a fraction (83 mg) containing the target chemical compound, (S)-hydroxymethyl 1,2,2-trimethyl-3-cyclopentenyl ketone. This decomposed partly in GC, so that no GC purity nor reduced GC yield of this compound could be determined.
¹H-NMR and ¹³C-NMR spectra on the main component of this fraction are identical to those of (S)-hydroxymethyl 1,2,2-trimethyl-3-cyclopentenyl ketone obtained in Example 7, and the fraction was 80:20 mixture of the target chemical compound and 1,2,2-trimethyl-3-cyclopentene-1-carboxylic acid, and a reduced NMR yield was 37%.

(R)-1,2,2-Trimethyl-3-cyclopenten-1-carboxylic Acid Synthesized Separately

Yellowish oil.
IR (D-ATR): ν=3042, 2967, 2937, 2875, 1699, 1618, 1461, 1411, 1369, 1337, 1309, 1279, 1211, 1076, 951, 745, 730, 715 cm⁻¹.
¹H-NMR (500 MHz, CDCl₃): δ=1.01 (3H, s), 1.15 (3H, s), 1.26 (3H, s), 2.03-2.08 (1H, dq-like m), 3.12-3.18 (1H, dt-like m), 5.33-5.37 (1H, m), 5.53-5.56 (1H, m), 11.93 (1H, COOH, br.) ppm.
¹³C-NMR (125 MHz, C₆D₆): δ=21.80, 22.01, 24.81, 41.67, 48.89, 54.72, 125.61, 139.11, 183.39 ppm.
GC-MS (EI, 70 eV): 41, 55, 67, 77, 93, 109 (base peak), 111, 125, 139, 154 (M*).
(S)-Hydroxymethyl 1,2,2-trimethyl-3-cyclopentenyl ketone synthesized above was placed in a sample bottle and stored at room temperature for a long period (83 days). Then, the purity of the target chemical compound-lowered to about 60%, as determined with ¹H-NMR.

Example 10: Synthesis of (R)-hydroxymethyl 1,2,2-trimethyl-3-cyclopentenyl ketone (Compound (R)-(3))

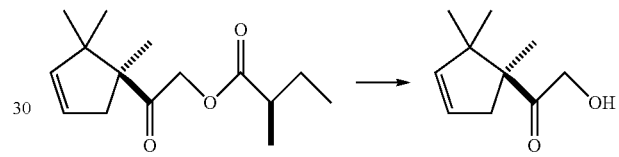

The procedures of Example 9 were repeated with the exception that 150 mg of (R)-2-(1,2,2-trimethyl-3-cyclopentenyl)-2-oxoethyl (R)-2-methylbutyrate synthesized as in Example 6 was used instead of (S)-2-(1,2,2-trimethyl-3-cyclopentenyl)-2-oxoethyl (S)-2-methylbutyrate, so that was obtained the target chemical compound, (R)-hydroxymethyl 1,2,2-trimethyl-3-cyclopentenyl ketone (100 mg, quantitative yield, gross). GC analysis failed to determine a purity of this compound due to partial thermal decomposition, but the NMR spectrum as described below indicates that this compound is almost pure.

(R)-Hydroxymethyl 1,2,2-trimethyl-3-cyclopentenyl ketone

Yellowish oil.
[α]_D²²–128.8° (c=1.04, CDCl₃)
The IR, ¹H-NMR, ¹³C-NMR, and GC-MS spectra of this compound were identical to those of (S)-hydroxymethyl 1,2,2-trimethyl-3-cyclopentenyl ketone obtained in Example 9.

Example 11: Synthesis of (S)-2-(1,2,2-trimethyl-3-cyclopentenyl)-2-oxoethyl isobutyrate (Compound (6): (S)-(6), R=isopropyl)

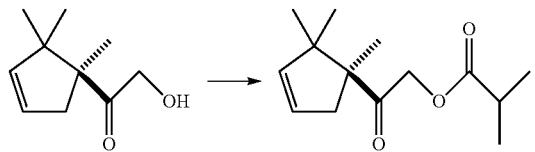 [SMILES: CC1(C)C=CC[C@]1(C)C(=O)CO ; CC(C)C(=O)OCC(=O)[C@@]1(C)CC=CC1(C)C]

Isobutyric anhydride (600 mg, compound (10), Y=R—C(=O)—, R=isopropyl) was added to a mixture of (S)-hydroxymethyl 1,2,2-trimethyl-3-cyclopentenyl ketone (90 mg) synthesized as in Example 9, pyridine (2.20 g), and methylene chloride (2 mL) in a nitrogen atmosphere. The reaction mixture was heated to 80° C. and stirred for 1.5 hours while distilling off methylene chloride, and further at room temperature for 13 hours. n-Hexane was added to the reaction mixture and the reaction was quenched with diluted hydrochloric acid. The concentrate obtained by ordinary post-treatment, i.e., washing, drying and concentration, was purified by silica gel column chromatography to obtain the target chemical compound, (S)-2-(1,2,2-trimethyl-3-cyclopentenyl)-2-oxoethyl isobutyrate (95 mg, 98.1% GC, yield 99%).

(S)-2-(1,2,2-Trimethyl-3-cyclopentenyl)-2-oxoethyl isobutyrate

Yellowish oil.

$[\alpha]_D^{26}$ –77.8° (c=1.00, CDCl$_3$)

IR (D-ATR): ν=3056, 2974, 2936, 2875, 1745, 1717, 1467, 1459, 1414, 1337, 1256, 1191, 1155, 1100, 1012, 748, 717 cm$^{-1}$.

$^1$H-NMR (500 MHz, CDCl$_3$): δ=0.92 (3H, s), 1.14 (3H, s), 1.20 (3H, s), 1.22 (3H, d, J=6.9 Hz), 1.23 (3H, d, J=7.0 Hz), 2.06-2.10 (1H, dq-like, J=16.4, 1.4 Hz), 2.68 (1H, sept, J=7.0 Hz), 3.07-3.11 (1H, dt-like, J=16.5, 2.3 Hz), 4.79 (1H, d, J=16.8 Hz), 4.85 (1H, d, J=16.8 Hz), 5.39-5.40 (1H, dq-like, J=5.8, 1.4 Hz), 5.59 (1H, ddd, J=2.3, 2.7, 5.8 Hz) ppm.

$^{13}$C-NMR (125 MHz, C$_6$D$_6$): δ=18.95, 18.97, 20.22.88, 24.32, 33.71, 40.93, 49.07, 58.61, 66.59, 125.68, 140.17, 176.53, 206.37 ppm.

GC-MS (EI, 70 eV): 43, 55, 71, 91, 109 (base peak), 122, 137, 150, 168, 180, 195, 209, 223, 238 (M$^+$).

Example 12: Synthesis of (S)-2-(1,2,2-trimethyl-3-cyclopentenyl)-2-oxoethyl acetate (6: (S)-(6), R=methyl)

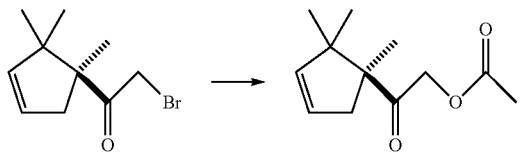

Acetyl chloride (100 mg, compound (10), Y=chlorine atom, R=methyl) was added to a mixture of (S)-hydroxymethyl 1,2,2-trimethyl-3-cyclopentenyl ketone (90 mg) synthesized as in Example 9, pyridine (0.20 g), and methylene chloride (2 mL) in a nitrogen atmosphere. The reaction mixture was stirred at room temperature for 5 hours, followed by addition of n-hexane. The reaction was quenched with diluted hydrochloric acid. The concentrate obtained by ordinary post-treatment, i.e., washing, drying and concentration, was purified by silica gel column chromatography to obtain the target chemical compound, (S)-2-(1,2,2-trimethyl-3-cyclopentenyl)-2-oxoethyl acetate (80 mg, 98.6% GC, yield 95%).

(S)-2-(1,2,2-Trimethyl-3-cyclopentenyl)-2-oxoethyl acetate

Yellowish oil.

$[\alpha]_D^{24}$ –96.6° (c=1.00, CDCl$_3$)

IR (D-ATR): ν=3054, 2964, 2936, 2872, 1752, 1717, 1459, 1415, 1372, 1276, 1231, 1185, 1133, 1077, 1023, 749, 718 cm$^{-1}$.

$^1$H-NMR (500 MHz, CDCl$_3$: δ=0.91 (3H, s), 1.14 (3H, s), 1.19 (3H, s), 2.06-2.10 (1H, dq-like, J=16.4, 1.4 Hz), 2.16 (3H, s), 3.06-3.10 (1H, dt-like, J=16.4, 2.3 Hz), 4.79 (1H, d, J=16.8 Hz), 4.85 (1H, d, J=16.8 Hz), 5.38-5.40 (1H, dq-like, J=5.8, 1.3 Hz), 5.59 (1H, ddd, J=2.3, 2.7, 5.9 Hz) ppm.

$^{13}$C-NMR (125 MHz, C$_6$D$_6$): δ=20.50, 20.90, 22.84, 24.31, 40.88, 49.11, 58.54, 66.85, 125.64, 140.12, 170.32, 206.37 ppm.

GC-MS (EI, 70 eV): 43, 55, 67, 81, 93, 109 (base peak), 122, 135, 150, 168, 181, 195, 210 (M$^+$).

Identification of the pheromones of ARMB will be described in detail hereinafter.

Analyzers and Conditions for Isolation and Identification

GC: Agilent 6890N, Injection: Split or Splitless 220° C., column: DB-23 0.25 mmφ×30 m, 60° C. (1 min)+10° C./min to 220° C. (8 min), or β-DEX(trade name) 120 0.25 mmφ× 30 m, 100° C. (5 min)+2° C./min to 180° C., carrier gas: He 1 mL/min, detector: FID 220° C.

GC-EAD: Hewlett-Packard HP5890 GC, amplifier: Nihon Koden AB-651J. A head of a male in an early stage of development was excised and connected to a ground electrode. A distal tip of an antenna comprising several nodes was cut, and the cut surface was connected to a capillary glass electrode of the EAD device with a drop of saline.

GC-MS: JEOL SX-102A, interface temperature 210° C., ion source temperature 220° C.

Preparative GC: programmable injector ATAS GL International OPTIC 3, fraction collection system Gerstel Gmbh & Co. KG; dry ice cooling.

Preparative HPLC: Hewlett-Packard HP1050, column: GL Science Intersil 4.6 mmφ×250 mm, particle size 5 m, room temperature, elution: 5% diethyl ether in hexane, 1.0 mL/min, detector: UV 210 nm.

NMR spectrometry: JEOL JNM-A600 spectrometer.

Collection of Volatile Substances

ARMB (*Pseudococcus baliteus*) was reared on a squash (*Cucurbita moschata*) fruit in a 16 h: 8 h bright-dark cycle, at 23° C., 50% humidity. The squash fruit was immersed in a 10 ppm methoprene solution for 0.5 minute to remove adult males. Then, the squash fruit accompanied with approximately 500 adult females was placed in a 1-L glass jar, and a headspace air was drawn via an activated carbon filter over the females and through an adsorbent (Alltech HayeSepQ 60/80 mesh 1 g) by a vacuum pump at a rate of 1 L/min. Adsorbed volatile substances were extracted with 15 mL of hexane every 3 or 4 days. The collection of volatile substances was continued for 6 weeks. The combined crude extracts were treated with 0.2 g of silica gel and subjected to preparative HPLC and preparative GC for isolation of pheromones.

Hydrogenation Reaction

A candidate Pheromone compound-(1 μg) was dissolved in ethanol (0.1 mL) and stirred in the presence of platinum black (5 mg) in a hydrogen gas atmosphere. After 10 minutes, the reaction mixture was centrifuged, and the supernatant (2 L) was analyzed by GC-MS.

Ethanolysis

A candidate pheromone compound-(10 μg) was dissolved in 0.01 M potassium hydroxide in ethanol (0.1 mL) in an argon gas atmosphere and left at 60° C. for 4 hours. The reaction mixture was neutralized and filtered by being let through an acidic ion exchange resin, Amberlite FCP3500 (2.5 g), which had been wetted with methanol and packed in a column, and then subjected to elution with methanol. The eluate was analyzed without further purification.

The invention claimed is:

1. A process for preparing a 2-(1,2,2-trimethyl-3-cyclopentenyl)-2-oxoethyl carboxylate compound of the following general formula (6):

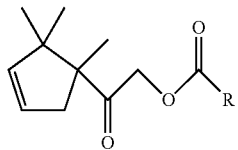

wherein R represents a monovalent hydrocarbon group having 1 to 9 carbon atoms, the process comprising:

esterifying a 2-(1,2,2-trimethyl-3-cyclopentenyl)-2-oxoethyl compound of the following general formula (5):

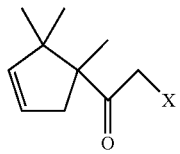

wherein X represents a hydroxyl group or a halogen atom, to form the 2-(1,2,2-trimethyl-3-cyclopentenyl)-2-oxoethyl carboxylate compound (6).

2. The process for preparing the 2-(1,2,2-trimethyl-3-cyclopentenyl)-2-oxoethyl carboxylate compound (6) according to claim 1, wherein the esterification is carried out with a halomethyl (1,2,2-trimethyl-3-cyclopentenyl) ketone compound of the following general formula (7):

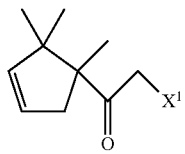

wherein $X^1$ represents a halogen atom,
and a carboxylic acid compound of the following general formula (8):

wherein R represents a monovalent hydrocarbon group having 1 to 9 carbon atoms.

3. A process for preparing hydroxymethyl 1,2,2-trimethyl-3-cyclopentenyl ketone of the following formula (3):

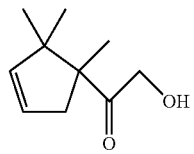

the process comprising
the process according to claim 1 for preparing the 2-(1,2,2-trimethyl-3-cyclopentenyl)-2-oxoethyl carboxylate compound (6), and
subjecting the 2-(1,2,2-trimethyl-3-cyclopentenyl)-2-oxoethyl carboxylate compound of the following general formula (6) to hydrolysis and/or alcoholysis to form hydroxymethyl 1,2,2-trimethyl-3-cyclopentenyl ketone (3).

4. A halomethyl (1,2,2-trimethyl-3-cyclopentenyl) ketone compound of the following general formula (7):

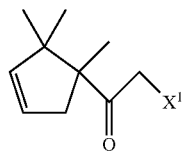

wherein $X^1$ represents a halogen atom.

5. A process for preparing hydroxymethyl 1,2,2-trimethyl-3-cyclopentenyl ketone of the following formula (3):

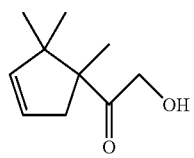

the process comprising
the process according to claim 2 for preparing the 2-(1,2,2-trimethyl-3-cyclopentenyl)-2-oxoethyl carboxylate compound (6), and
subjecting the 2-(1,2,2-trimethyl-3-cyclopentenyl)-2-oxoethyl carboxylate compound of the following general formula (6) to hydrolysis and/or alcoholysis to form hydroxymethyl 1,2,2-trimethyl-3-cyclopentenyl ketone (3).

* * * * *

UNITED STATES PATENT AND TRADEMARK OFFICE
CERTIFICATE OF CORRECTION

Page 1 of 2

PATENT NO. : 11,530,176 B2
APPLICATION NO. : 17/071013
DATED : December 20, 2022
INVENTOR(S) : Kinsho et al.

It is certified that error appears in the above-identified patent and that said Letters Patent is hereby corrected as shown below:

In the Specification

Column 10, Line 36: Please correct "($C_2$)" to read --($Cl_2$)--

Column 10, Line 37: Please correct "(IC)" to read --(ICl)--

Column 12, Line 34: Please correct "($Cr_2Cl_2$)" to read --($CrO_2Cl_2$)--

Column 25, Lines 50-55: Please correct " 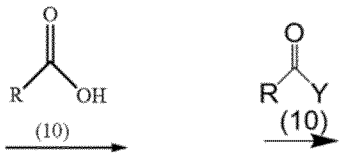 " to read -- -HY --

Column 28, Line 35: Please correct "X and R" to read --$X^1$ and R--

Column 31, Line 54: Please correct "1000" to read --100%--

Column 31, Line 58: Please correct "product]+" to read --product]÷--

Column 34, Line 53: Please correct "717 $cm^1$" to read --717 $cm^{-1}$--

Column 34, Line 64: Please correct "6=4.54" to read --δ=4.54--

Column 35, Line 6: Please correct "2 of the" to read --2 µl of the--

Column 35, Line 67: Please correct "6=4.53" to read --δ=4.53--

Column 36, Line 10: Please correct "(M)" to read --($M^+$)--

Signed and Sealed this
Sixth Day of June, 2023

Katherine Kelly Vidal
*Director of the United States Patent and Trademark Office*

CERTIFICATE OF CORRECTION (continued)
U.S. Pat. No. 11,530,176 B2

Column 39, Line 29: Please correct "6=0.99" to read --$\delta$=0.99--

Column 42, Line 14: Please correct "(M*)" to read --(M$^+$)--

Column 44, Line 42: Please correct "5 m" to read --5 μm--

Column 44, Line 67: Please correct "(2 L)" to read --(2 μL)--